US010239825B2

(12) United States Patent
Sleigh et al.

(10) Patent No.: US 10,239,825 B2
(45) Date of Patent: Mar. 26, 2019

(54) KETAMINE DERIVATIVES

(71) Applicant: Auckland Uniservices Limited, Auckland (NZ)

(72) Inventors: James Wallace Sleigh, Hamilton (NZ); William Alexander Denny, Auckland (NZ); Jiney Jose, Auckland (NZ); Swarnalatha Akuratiya Gamage, Auckland (NZ); Martyn Gregory Harvey, Hamilton (NZ); Logan James Voss, Hamilton (NZ)

(73) Assignee: Auckland Uniservices Limited, Auckland (NZ)

( * ) Notice: Subject to any disclaimer, the term of this patent is extended or adjusted under 35 U.S.C. 154(b) by 0 days.

(21) Appl. No.: 15/463,532

(22) Filed: Mar. 20, 2017

(65) Prior Publication Data

US 2017/0190653 A1 Jul. 6, 2017

Related U.S. Application Data

(63) Continuation of application No. 14/433,957, filed as application No. PCT/IB2013/059191 on Oct. 8, 2013, now abandoned.

(51) Int. Cl.
*C07C 229/14* (2006.01)
*C07C 229/46* (2006.01)
*C07C 225/20* (2006.01)

(52) U.S. Cl.
CPC .......... *C07C 229/14* (2013.01); *C07C 225/20* (2013.01); *C07C 229/46* (2013.01)

(58) Field of Classification Search
CPC ............................. C07C 229/14; C07C 225/20
See application file for complete search history.

(56) References Cited

U.S. PATENT DOCUMENTS

| | | | |
|---|---|---|---|
| 3,254,124 A | 5/1966 | Stevens | |
| 5,019,583 A | 5/1991 | Feldman et al. | |
| 5,466,700 A | 11/1995 | Batenhorst et al. | |
| 5,866,591 A | 2/1999 | Gatlin et al. | |
| 7,371,829 B2 | 5/2008 | McConnell et al. | |
| 7,638,651 B2 | 12/2009 | Gant et al. | |
| 2004/0248963 A1 | 12/2004 | Crooks et al. | |
| 2004/0248964 A1* | 12/2004 | Crooks ................ | A61K 31/165 514/417 |
| 2008/0268071 A1 | 10/2008 | Gant et al. | |
| 2014/0296241 A1 | 10/2014 | Wainer et al. | |

FOREIGN PATENT DOCUMENTS

| | | |
|---|---|---|
| EP | 1333023 | 8/2003 |
| WO | 2004045601 | 6/2004 |
| WO | 2007038949 | 4/2007 |

OTHER PUBLICATIONS

M. Carstensen et al., "Adding ketamine to morphine for intravenous patient-controlled analgesia for acute oostoperative pain: a qualitative review of randomized trials," British Journal of Anaesthesia 104(4): 401-6 (2010).
J.Y. Domoradzki et al., "Hydrolysis Kinetics of Propylene Glycol Monomethyl Ether Acetate in Rats in Vivo and in Rat and Human Tissues in Vitro," Toxicological Sciences 75, 31-39 (2003).
L.Y. Leung et al., "Comparative Pharmacology in the rat of Ketamine and Its two Principal Metabolites, Norketamine and (Z)-6-Hydroxynorketamine," Journal of Medicinal Chemistry, vol. 29, No. 11, 2396-2399 (1986).
H.A. Adams et al., "Vam Razemat zum Eutomer: (S)-Ketamin," Der Anaesthesist, 46: 1026-1042 (1997).
E. Visser et al., "The role of ketamine in pain management," Biomedicine & Pharmacotherapy 60, 341-348 (2006).
J.F. Cotten et al., "A Novel Rapidly Metabolized and Ultra-short-acting Etomidate Analogue that Does Not Produce Prolonged Adrenocortical Suppression," Anesthesiology, vol. 11, No. 2, 240-249 (Aug. 2009).
K. Hirota et al., "Ketamine: its mechanism(s) of action and unusual clinical uses," British Journal of Anaesthesia, vol. 77, No. 4, 441-444 (Oct. 1996).
G. Volgyi et al., "Potentiometric and spectrophotometric pKa determination of water-insoluble compounds: Validation study in a new cosolvent system," Analytica Chimica Acta 583, 418-428 (2007).
R.F. Parcell et al., "Synthesis of Ketamine Metabolites I and II and Some Anomalous Reactions of 6-Bromoketamine," The Journal of Organic Chemistry, vol. 47, No. 25, 5055-560 (Dec. 1981).
K. Laskowski et al., "A systematic review of intravenous ketamine for postoperative analgesia," Canadian Anesthesiologists' Society 58: 911-923 (2011).
S.C. Hong et al., "Stereochemical Studies of Demethylated Ketamine Enantiomers," Journal of Pharmaceutical Sciences, vol. 71, No. 8, 912-914 (Aug. 1982).
E.F. Domino, "Taming the Ketamine Tiger," Anesthesiology, vol. 113, No. 3, 678-684 (2010).
A. Chiaretti et al., "Comparison of Propofol Versus Propofol-Ketamine Combination in Pediatric Oncologic Procedures Performed by Non-Anesthesiologists," Pediatr Blood Cancer, 57: 1163-1167 (2011).
S. Buitrago et al., "Safety and Efficacy of Various Combinations of Injectable Anesthetics in BALB/c Mice," Journal of the American Association for Laboratory Animal Science, vol. 47, No. 1, Jan. 11-17, 2008.
M.E. Fox et al., "A Convergent Synthesis of the 11-Oxa Prostaglandin Analogue AL-12182," Journal of Organic chemistry, vol. 70, No. 4, 1227-1236 (2005).
Z.P. Demko et al., "An Intramolecular [2 + 3] Cycloaddition Route to Fused 5-Heterosubstituted Tetrazoles," Organic Letters, vol. 3, No. 25, 4091-4094 (2001).

(Continued)

*Primary Examiner* — Pancham Bakshi
(74) *Attorney, Agent, or Firm* — Dann, Dorfman, Herrell & Skillman, P.C.

(57) ABSTRACT

The present invention relates to ketamine derivatives of the formula (I), pharmaceutical compositions comprising them, and methods for treating pain comprising administering them, and their use in the manufacture of medicaments for treating pain. The present invention also relates to methods for anaesthetizing and methods for sedating a subject comprising administering ketamine derivatives of the formula (II).

24 Claims, 3 Drawing Sheets

(56) References Cited

OTHER PUBLICATIONS

International Search Report and Written Opinion of the International Searching Authority, PCT/IB2013/059191, Jan. 17, 2014, pp. 1-10.
International Preliminary Report on Patentability, PCT/IB2013/059191, dated Apr. 9, 2015, pp. 1-6.
NZ First Examination Report, IP No. 619257, dated Jan. 8, 2014, pp. 1-2.
NZ Notice of Acceptance, IP No. 619257, dated Jul. 14, 2015.
J. Jose et al., "Structure-activity relationships for ketamine esters as short-acting anaesthetics," Bioorganic & Medicinal Chemistry, 21 (2013) 5098-5106.
M. Harvey et al., "Development of Rapidly Metabolized and Ultra-Short-Acting Ketamine Analogs," Anesthesia and Analgesia, vol. 121, No. 4 (Oct. 2015).
T.D. Gould et al., "Ketamine Mechanism of Action: Separating the Wheat from the Chaff," Neuropsychopharmacology, (2017) 42, 368-369.
D.W. Herd et al., "Modeling the norketamine metabolite in children and the implications for analgesia," Pediatric Anesthesia 2007, 17: 831-840 (2007).
Zawilska, J.B., "Methoxetamine—a novel recreational drug with potent hallucinogenic properties," Toxicology Letters 230 (2014) 402-407.
Moghimi, A. et al., "Synthesis of 2-(2-Fluorophenyl)-2-Methylamino-Cyclohexanone as a new Ketamine Derivative," Synthetic Communications, 44: 2021-2028, 2014.
Lee, C.-H. et al., "NMDA receptor structures reveal subunit arrangement and pore architecture," Nature, vol. 511, 2014, 191-210.
Kohrs, R. et al., "Ketamine: Teaching an Old Drug New Tricks," Anesth Analg 1998, 87: 1186-93.
Kjellgren, A. et al., "Methoxetamine (MXE)—A Phenomenological Study of Experiences Induced by a 'Legal High' from the Internet," Journal of Psychoactive Drugs, 45 (3), 276-286, 2013.
Sleigh, J. et al., "Ketamine—More mechanisms of action than just NMDA blockade," Trends in Anaesthesia and Critical Care 4 (2014) 76-81.
Harvey, M. et al., "Determination of the Hypnotic Potency in Rats of the Novel Ketamine Ester Analogue SN 35210," Pharmacology 2015; 96:226-232.
Patani, G. A. et al., "Bioisosterism: A Rational Approach in Drug Design," Chem. Rev. 1996, 96, 3147-3176.
Frison, G. et al., "Characterization of the designer drug deschloroketamine (2-methylamino-2-phenylcyclohexanone) by gas chromatography/mass spectrometry, liquid chromatography/high-resolution mass spectrometry, multistage mass spectrometry, and nuclear magnetic resonance," Rapid Commun. Mass Spectrom. 2016, 30, 151-160.
Wang, S. et al., "Synthesis of anesthetic active substance monofluoroamine," Acta Scientiarum Naturalium, Universitatis Pekinensis (2), 1987 (Chinese and English versions).

\* cited by examiner

US 10,239,825 B2

KETAMINE DERIVATIVES

CROSS REFERENCE TO RELATED APPLICATIONS

This application is a continuation of application Ser. No. 14/433,957, filed Apr. 7, 2015, which is the national stage of International Application No. PCT/IB2013/059191, filed Oct. 8, 2013, the entireties of which are incorporated herein by reference.

TECHNICAL FIELD

The present invention relates to ketamine derivatives, pharmaceutical compositions comprising them, and their use as anaesthetics, analgesics, or sedatives.

BACKGROUND OF THE INVENTION (2-o-Chlorophenyl)-2-methylamino-cyclohexanone (ketamine) is an effective non-opioid anaesthetic/analgesic drug [Laskowski et al., Can J Anesth 2011, 58, 911: Carstensen & Møller, Br J Anaesth. 2010, 104, 401], with the major advantages over opioids in that it shows no respiratory depression or hyperalgesic effects, and is also free of longer-term effects such as increased tolerance and immune suppression.

Ketamine is normally used as the racemate, but more recently the more active (S)-enantiomer has begun to be employed. (S)-Ketamine has similar pharmacological, analgesic and anaesthetic properties to the racemate, but is about twice as potent [Adams & Werner, Anaesthetist 1997, 46, 1026].

(S)-ketamine

The most important adverse effect of ketamine is its hallucinogenic properties which, together with its relatively long half-life (2-3 h) means that it is normally administered together with sedative or hypnotic drugs like midazolam and/or propofol to control the prolonged period of post-anesthesia hallucinations [Domino, Anesthesiology 2010, 113, 678, Chiaretti et al., Pediatric Blood & Cancer 2011, 57, 1163]. While (S)-ketamine has somewhat faster elimination [Adams & Werner, Anaesthetist 1997, 46, 1026], there is still a need for analogues with much shorter half-lives to avoid the concomitant use of sedatives/hypnotics.

It is an object of the present invention to go some way to meeting this need, and/or to at least provide the public with a useful choice.

Other objects of the invention may become apparent from the following description which is given by way of example only.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date.

SUMMARY OF THE INVENTION

In one aspect, the present invention provides a compound of formula (I):

(I)

wherein $Y^1$ is —$C_{2-6}$aliphaticC(O)O$R^1$, —$C_{2-6}$aliphaticOC(O)$R^1$, —$C_{1-6}$aliphaticC(O)O$C_{1-6}$aliphaticC(O)O$R^1$, or —$C_{1-6}$aliphaticC(O)O$C_{1-6}$aliphatic$R^3$, wherein each aliphatic is optionally substituted with one or more $R^2$;

$R^1$ is $C_{1-6}$aliphatic, optionally substituted with one or more halo, CN, $NO_2$, $NH_2$, $NHR^{11}$, $NR^{11}R^{12}$, $C_{1-6}$haloalkyl, $C_{1-6}$haloalkoxy, C(O)$NH_2$, C(O)$NHR^{11}$, C(O)$NR^{11}R^{12}$, $SO_2R^{11}$, $OR^{11}$, C(O)$R^{11}$, and $C_{1-6}$aliphatic;

$R^2$ is $C_{1-6}$aliphatic, optionally substituted with one or more halo, $OR^{11}$, or CN;

$R^3$ is hydrogen or $R^1$;

$R^{11}$ and $R^{12}$ are each independently $C_{1-6}$aliphatic; or $R^{11}$ and $R^{12}$ together with the nitrogen atom to which they are attached are a heteroaryl or heterocyclyl ring;

$Y^2$ is hydrogen or $R^2$;

$X^1$ and $X^2$ are each independently hydrogen, $R^2$, halo, $NO_2$, $NH_2$, $NHR^{11}$, $NR^{11}R^{12}$, $C_{1-6}$haloalkyl, $C_{1-6}$haloalkoxy, C(O)$NH_2$, C(O)$NHR^{11}$, C(O)$NR^{11}R^{12}$, $SO_2R^{11}$, $OR^{11}$, C(O)$R^{11}$, $C_{1-6}$aliphatic$Y^1$, $OY^1$, C(O)$Y^1$, $SO_2Y^1$, or C(O)$NHY^1$ at any of the available 2-5 positions;

or a pharmaceutically acceptable salt or solvate thereof.

In another aspect, the present invention provides a pharmaceutical composition comprising a compound of formula (I) or a pharmaceutically acceptable salt or solvate thereof, and a pharmaceutically acceptable diluent, excipient, or carrier.

In another aspect, the present invention provides a method for treating pain in a subject in need thereof, the method comprising administering a therapeutically effective amount of a compound of formula (I) to the subject.

In another aspect, the invention provides use of a compound of formula (I) in the manufacture of a medicament for treating pain.

In another aspect, the invention provides a compound of formula (I) for treating pain.

In one embodiment, the method, medicament, or compound for treating pain is for providing analgesia.

In another aspect, the present invention provides a method for anaesthetizing a subject in need thereof, the method comprising administering a therapeutically effective amount of a compound of formula (II) to the subject:

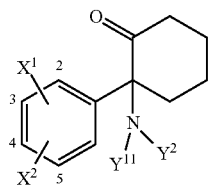

wherein

Y$^1$ is —C$_{1-6}$aliphaticC(O)OR$^1$, —C$_{1-6}$aliphaticOC(O)R$^1$, —C$_{1-6}$aliphaticC(O)OC$_{1-6}$aliphaticC(O)OR$^1$, or —C$_{1-6}$aliphaticC(O)OC$_{1-6}$aliphaticOR$^3$, wherein each aliphatic is optionally substituted with one or more R$^2$; and R$^1$, R$^2$, R$^3$, Y$^2$, X$^1$, and X$^2$ are as defined in the compound of formula (I);

or a pharmaceutically acceptable salt or solvate thereof.

In one embodiment, the method is for anaesthetizing a subject for a surgical procedure.

In some embodiments, the method is for inducing general anaesthesia. In other embodiments, the method is for inducing and maintaining general anaesthesia.

In another aspect, the present invention provides use of a compound of formula (II) in the manufacture of a medicament for providing anaesthesia.

In one embodiment, the medicament is for providing anaesthesia for a surgical procedure.

In some embodiments, the medicament is for inducing general anaesthesia. In other embodiments, the medicament is for inducing and maintaining general anaesthesia.

In another aspect, the present invention provides a compound of formula (II) for providing anaesthesia.

In one embodiment, the compound is for providing anaesthesia for a surgical procedure.

In some embodiments, the compound is for inducing general anaesthesia. In other embodiments, the compound is for inducing and maintaining general anaesthesia.

In another aspect, the present invention provides a method for sedating a subject in need thereof, the method comprising administering a therapeutically effective amount of a compound of the formula (II) to the subject.

In one embodiment, the method is for sedating a subject for a medical procedure. In some embodiments, method is for providing conscious sedation.

In some embodiments, the method is for inducing conscious sedation. In other embodiments, the method is for inducing and maintaining conscious sedation.

In another aspect, the present invention provides use of a compound of formula (II) in the manufacture of a medicament for providing sedation.

In one embodiment, the medicament is for providing sedation for a medical procedure. In some embodiments, the medicament is for providing conscious sedation.

In some embodiments, the medicament is for inducing conscious sedation. In other embodiments, the medicament is for inducing and maintaining conscious sedation.

In another aspect, the present invention provides a compound of formula (II) for providing sedation.

In one embodiment, the compound is for providing sedation is for a medical procedure. In some embodiments, the compound is for providing conscious sedation.

In some embodiments, the compound is for inducing conscious sedation. In other embodiments, the compound is for inducing and maintaining conscious sedation.

The following embodiments relate to the compounds of formula (I) and (II), as appropriate.

In one embodiment, Y$^1$ is —C$_{2-6}$alkylC(O)OR$^1$, —C$_{2-6}$alkylOC(O)R$^1$, —C$_{1-6}$alkylC(O)OC$_{1-6}$alkylC(O)OR$^1$, or —C$_{1-6}$alkylC(O)OC$_{1-6}$alkylOR$^3$, wherein each alkyl is optionally substituted.

In another embodiment, Y$^1$ is —C$_{2-6}$alkylC(O)OR$^1$ or —C$_{1-6}$alkylC(O)OC$_{1-6}$alkylC(O)OR$^1$, wherein each alkyl is optionally substituted. In one exemplary embodiment, Y$^1$ is —C$_{2-6}$alkylC(O)OR$^1$, wherein the alkyl is optionally substituted. In one specifically contemplated embodiment, Y$^1$ is —C$_{2-6}$alkylC(O)OR$^1$.

In one embodiment, Y$^{11}$ is —C$_{1-6}$alkylC(O)OR$^1$, —C$_{1-6}$alkylOC(O)R$^1$, —C$_{1-6}$alkylC(O)OC$_{1-6}$alkylC(O)OR$^1$, or —C$_{1-6}$alkylC(O)OC$_{1-6}$alkylOR$^3$, wherein each alkyl is optionally substituted. In another embodiment, Y$^{11}$ is —C$_{1-6}$alkylC(O)OR$^1$ or —C$_{1-6}$alkylC(O)OC$_{1-6}$alkylC(O)OR$^1$, wherein each alkyl is optionally substituted. In one exemplary embodiment, Y$^{11}$ is —C$_{1-6}$alkylC(O)OR$^1$, wherein the alkyl is optionally substituted. In one specifically contemplated embodiment, Y$^{11}$ is —C$_{1-6}$alkylC(O)OR$^1$.

In some embodiments, each alkyl in Y$^1$ or Y$^{11}$ is optionally substituted with from one to three R$^2$. In certain embodiments, each alkyl in Y$^1$ or Y$^{11}$ is optionally substituted with one or two R$^2$.

In one embodiment, R$^1$ is C$_{1-6}$alkyl, C$_{2-6}$alkenyl, cycloalkyl, or cycloalkenyl, wherein each alkyl, alkenyl, cycloalkyl, and cycloalkenyl are optionally substituted with one or more halo, CN, NO$_2$, NH$_2$, NHR$^{11}$, NR$^{11}$R$^{12}$, C$_{1-6}$haloalkyl, C$_{1-6}$haloalkoxy, C(O)NH$_2$, C(O)NHR$^{11}$, C(O)NR$^{11}$R$^{12}$, SO$_2$R$^{11}$, OR$^{11}$, and C(O)R$^{11}$; and each alkyl and alkenyl is optionally substituted with one or more cycloalkyl or cycloalkenyl; and each cycloalkyl and cycloalkenyl is optionally substituted with one or more C$_{1-6}$alkyl or C$_{2-6}$alkenyl.

In one embodiment, R$^1$ is C$_{1-6}$alkyl, C$_{2-6}$alkenyl, cycloalkyl, or cycloalkenyl, wherein each alkyl and cycloalkyl are optionally substituted with one or more halo, CN, NO$_2$, NH$_2$, NHR$^1$, NR$^{11}$R$^{12}$, C$_{1-6}$haloalkyl, C$_{1-6}$haloalkoxy, C(O)NH$_2$, C(O)NHR$^{11}$, C(O)NR$^{11}$R$^{12}$, SO$_2$R$^{11}$, OR$^{11}$, and C(O)R$^{11}$; and each alkyl is optionally substituted with cycloalkyl or cycloalkenyl; and each cycloalkyl is optionally substituted with C$_{1-6}$alkyl or C$_{2-6}$alkenyl.

In one embodiment, R$^1$ is C$_{2-6}$alkenyl or cycloalkenyl, wherein each alkenyl and cycloalkenyl are optionally substituted with one or more halo, CN, NO$_2$, NH$_2$, NHR$^{11}$, NR$^{11}$R$^{12}$, C$_{1-6}$haloalkyl, C$_{1-6}$haloalkoxy, C(O)NH$_2$, C(O)NHR$^{11}$, C(O)NR$^{11}$R$^{12}$, SO$_2$R$^{11}$, OR$^{11}$, and C(O)R$^{11}$; and each alkyl is optionally substituted with cycloalkyl or cycloalkenyl; and each cycloalkyl is optionally substituted with C$_{1-6}$alkyl or C$_{2-6}$alkenyl.

In other embodiment, R$^1$ is C$_{1-6}$alkyl or cycloalkyl, wherein each alkyl and cycloalkyl is optionally substituted. In one exemplary embodiment R$^1$ is C$_{1-6}$alkyl, wherein each alkyl is optionally substituted. In one specifically contemplated embodiment R$^1$ is C$_{1-6}$alkyl.

In some embodiments, each alkyl or cycloalkyl in R$^1$ is optionally substituted with from one to three optional substituents. In certain embodiments, each alkyl or cycloalkyl in R$^1$ is optionally substituted with one or two optional substituents.

In some embodiment, R$^2$ is C$_{1-6}$alkyl or cycloalkyl, optionally substituted with one or more halo, OR$^{11}$, or CN. In other embodiments, R$^2$ is C$_{1-6}$alkyl, optionally substituted with one or more halo, OR$^{11}$, or CN. In certain exemplary embodiments, R$^2$ is C$_{1-6}$alkyl.

In some embodiments, $R^{11}$ and $R^{12}$ are each independently $C_{1-6}$alkyl, $C_{2-6}$alkenyl, cycloalkyl, or cycloalkenyl; or $R^{11}$ and $R^{12}$ together with the nitrogen atom to which they are attached are a heteroaryl or heterocyclyl ring. In other embodiments, $R^{11}$ and $R^{12}$ are each independently $C_{1-6}$alkyl or cycloalkyl; or $R^{11}$ and $R^{12}$ together with the nitrogen atom to which they are attached are a heteroaryl or heterocyclyl ring. In certain embodiments, $R^{11}$ and $R^{12}$ are $C_{1-6}$alkyl.

In one embodiment, $Y^2$ is hydrogen or $C_{1-6}$alkyl, wherein the alkyl is optionally substituted. In one exemplary embodiment, $Y^2$ is hydrogen or $C_{1-6}$alkyl. In one specifically contemplated embodiment, $Y^2$ is hydrogen. In another specifically contemplated embodiment, $Y^2$ is hydrogen or methyl.

In some embodiments, $X^1$ and $X^2$ are each independently hydrogen, $R^2$, halo, $NO_2$, $NH_2$, $NHR^{11}$, $NR^{11}R^{12}$, $C_{1-6}$haloalkyl, $C_{1-6}$haloalkoxy, $C(O)NH_2$, $C(O)NHR^{11}$, $C(O)NR^{11}R^{12}$, $SO_2R^{11}$, $OR^{11}$, $C(O)R^{11}$, $C_{1-6}$alkylY$^1$, $OY^1$, $C(O)Y^1$, $SO_2Y^1$, or $C(O)NHY^1$ at any of the available 2-5 positions.

In some embodiments, $X^1$ and $X^2$ are each independently hydrogen, $R^2$, halo, $NO_2$, $NH_2$, $NHR^{11}$, $NR^{11}R^{12}$, $C_{1-6}$haloalkyl, $C_{1-6}$haloalkoxy, $C(O)NH_2$, $C(O)NHR^{11}$, $C(O)NR^{11}R^{12}$, $SO_2R^{11}$, $OR^{11}$, or $C(O)R^{11}$ at any of the available 2-5 positions.

In some embodiments, $X^1$ and $X^2$ are each independently hydrogen, $R^2$, halo, $NO_2$, $NH_2$, $NHR^{11}$, $NR^{11}R^{12}$, $C_{1-6}$haloalkyl, $C_{1-6}$haloalkoxy, $C(O)NH_2$, $C(O)NHR^{11}$, $C(O)NR^{11}R^{12}$, $SO_2R^{11}$, $OR^{11}$, or $C(O)R^{11}$; or $X^2$ is $C_{1-6}$alkylY$^1$, $OY^1$, $C(O)Y^1$, $SO_2Y^1$, or $C(O)NHY^1$ at any of the available 2-5 positions.

In some embodiments, $X^1$ and $X^2$ are each independently hydrogen, $R^2$, halo, $NO_2$, $NH_2$, $NHR^{11}$, $NR^{11}R^{12}$, $C_{1-6}$haloalkyl, $C_{1-6}$haloalkoxy, $C(O)NH_2$, $C(O)NHR^{11}$, $C(O)NR^{11}R^{12}$, $SO_2R^{11}$, $OR^{11}$, or $C(O)R^{11}$ at any of the available 2-5 positions.

In one embodiment, $X^1$ and $X^2$ are each independently hydrogen, $R^2$, halo, $C_{1-6}$haloalkyl, $C_{1-6}$haloalkoxy, $SO_2R^{11}$, $OR^{11}$, or $C(O)R^{11}$; or $X^2$ is $C_{1-6}$alkylY$^1$, $OY^1$, $C(O)Y^1$, or $SO_2Y^1$ at any of the available 2-5 positions.

In one embodiment, $X^1$ and $X^2$ are each independently hydrogen, $R^2$, halo, $C_{1-6}$haloalkyl, $C_{1-6}$haloalkoxy, $SO_2R^{11}$, $OR^{11}$, or $C(O)R^{11}$ at any of the available 2-5 positions.

In one embodiment, $X^1$ and $X^2$ are each independently hydrogen, $R^2$, halo, $C_{1-6}$haloalkyl, $C_{1-6}$haloalkoxy, $SO_2R^{11}$, or $OR^{11}$ at any of the available 2-5 positions.

In one embodiment, $X^1$ and $X^2$ are each independently hydrogen, $R^2$, halo, $C_{1-6}$haloalkyl, $C_{1-6}$haloalkoxy, $SO_2R^{11}$, or $OR^{11}$ at any of the available 2-5 positions.

In one embodiment, $X^1$ is halo; and $X^2$ is independently hydrogen, $R^2$, halo, $C_{1-6}$haloalkyl, $C_{1-6}$haloalkoxy, $SO_2R^{11}$, or $OR^{11}$ at any of the available 2-5 positions.

In one embodiment, $X^1$ is 2-halo. In another embodiment, $X^1$ is 2-chloro.

In one embodiment, $X^1$ is 2-chloro; and $X^2$ is hydrogen, $R^2$, halo, $C_{1-6}$haloalkyl, $C_{1-6}$haloalkoxy, $SO_2R^{11}$, or $OR^{11}$ at any of positions 3-5.

In some embodiments, the $C_{1-6}$haloalkyl is $CF_3$, $CHF_2$, or $CH_2F$. In certain embodiments, the $C_{1-6}$haloalkyl is $CF_3$. In some embodiments, the $C_{1-6}$haloalkoxy is $OCF_3$, $OCHF_2$, or $OCH_2F$. In certain embodiments, the $C_{1-6}$haloalkoxy is $CF_3$.

In some embodiments, the halo is F, Cl, or Br. In certain embodiments, the halo is F or Cl.

In one embodiment, $Y^1$ is $—C_{2-6}$alkylC(O)OR$^1$, $—C_{2-6}$alkylOC(O)R$^1$, $—C_{1-6}$alkylC(O)OC$_{1-6}$alkylC(O)OR$^1$, or $—C_{1-6}$alkylC(O)OC$_{1-6}$alkylOR$^3$, wherein each alkyl is optionally substituted with one or more $R^2$; $R^1$ is $C_{1-6}$alkyl, $C_{2-6}$alkenyl, cycloalkyl, or cycloalkenyl, wherein each alkyl and cycloalkyl are optionally substituted with one or more halo, CN, $NO_2$, $NH_2$, $NHR^{11}$, $NR^{11}R^{12}$, $C_{1-6}$haloalkyl, $C_{1-6}$haloalkoxy, $C(O)NH_2$, $C(O)NHR^{11}$, $C(O)NR^{11}R^{12}$, $SO_2R^{11}$, $OR^{11}$, and $C(O)R^{11}$; and each alkyl is optionally substituted with cycloalkyl or cycloalkenyl; and each cycloalkyl is optionally substituted with $C_{1-6}$alkyl or $C_{2-6}$alkenyl; $R^2$ is $C_{1-6}$alkyl or cycloalkyl, optionally substituted with one or more halo, $OR^{11}$, or CN; $R^{11}$ and $R^{12}$ are each independently $C_{1-6}$alkyl, $C_{2-6}$alkenyl, cycloalkyl, or cycloalkenyl; or $R^{11}$ and $R^{12}$ together with the nitrogen atom to which they are attached are a heteroaryl or heterocyclyl ring; and $X^1$ and $X^2$ are each independently hydrogen, $R^2$, halo, $NO_2$, $NH_2$, $NHR^{11}$, $NR^{11}R^{12}$, $C_{1-6}$haloalkyl, $C_{1-6}$haloalkoxy, $C(O)NH_2$, $C(O)NHR^{11}$, $C(O)NR^{11}R^{12}$, $SO_2R^{11}$, $OR^{11}$, $C(O)R^{11}$, $C_{1-6}$alkylY$^1$, $OY^1$, $C(O)Y^1$, $SO_2Y^1$, or $C(O)NHY^1$ at any of the available 2-5 positions.

In one embodiment, $Y^{11}$ is $—C_{1-6}$alkylC(O)OR$^1$, $—C_{1-6}$alkylOC(O)R$^1$, $—C_{1-6}$alkylC(O)OC$_{1-6}$alkylC(O)OR$^1$, or $—C_{1-6}$alkylC(O)OC$_{1-6}$alkylOR$^3$, wherein each alkyl is optionally substituted with one or more $R^2$; $R^1$ is $C_{1-6}$alkyl, $C_{2-6}$alkenyl, cycloalkyl, or cycloalkenyl, wherein each alkyl and cycloalkyl are optionally substituted with one or more halo, CN, $NO_2$, $NH_2$, $NHR^{11}$, $NR^{11}R^{12}$, $C_{1-6}$haloalkyl, $C_{1-6}$haloalkoxy, $C(O)NH_2$, $C(O)NHR^{11}$, $C(O)NR^{11}R^{12}$, $SO_2R^{11}$, $OR^{11}$, and $C(O)R^{11}$; and each alkyl is optionally substituted with cycloalkyl or cycloalkenyl; and each cycloalkyl is optionally substituted with $C_{1-6}$alkyl or $C_{2-6}$alkenyl; $R^2$ is $C_{1-6}$alkyl or cycloalkyl, optionally substituted with one or more halo, $OR^{11}$, or CN; $R^{11}$ and $R^{12}$ are each independently $C_{1-6}$alkyl, $C_{2-6}$alkenyl, cycloalkyl, or cycloalkenyl; or $R^{11}$ and $R^{12}$ together with the nitrogen atom to which they are attached are a heteroaryl or heterocyclyl ring; and $X^1$ and $X^2$ are each independently hydrogen, $R^2$, halo, $NO_2$, $NH_2$, $NHR^{11}$, $NR^{11}R^{12}$, $C_{1-6}$haloalkyl, $C_{1-6}$haloalkoxy, $C(O)NH_2$, $C(O)NHR^{11}$, $C(O)NR^{11}R^{12}$, $SO_2R^{11}$, $OR^{11}$, $C(O)R^{11}$, $C_{1-6}$alkylY$^1$, $OY^1$, $C(O)Y^1$, $SO_2Y^1$, or $C(O)NHY^1$ at any of the available 2-5 positions.

In one embodiment, $Y^1$ is $—(CR^AR^B)_m(CR^CR^D)_nC(O)OR^1$, $—(CR^AR^B)_m(CR^CR^D)_nOC(O)R^1$, $—(CR^AR^B)_{m-1}(CR^CR^D)_nC(O)O(CR^GR^H)_p(CR^ER^F)_oC(O)OR^1$, or $—(CR^AR^B)_{m-1}(CR^CR^D)_nC(O)O(CR^GR^H)_p(CR^ER^F)_oOR^3$; m is an integer from 2 to 6; o is an integer from 1 to 6; n and p are each independently 0 or 1; the sum of m and n and the sum of o and p is 6 or less; and $R^A$, $R^B$, $R^C$, $R^D$, $R^E$, $R^F$, $R^G$, and $R^H$ at each instance of m, n, o, and p are each independently hydrogen or $R^2$.

In one embodiment, $Y^{11}$ is $—(CR^AR^B)_m(CR^CR^D)_nC(O)OR^1$, $—(CR^AR^B)_m(CR^CR^D)_nOC(O)R^1$, $—(CR^AR^B)_m(CR^CR^D)_nC(O)O(CR^GR^H)_p(CR^ER^F)_oC(O)OR^1$, or $—(CR^AR^B)_m(CR^CR^D)_nC(O)O(CR^GR^H)_p(CR^ER^F)_oOR^3$; m and o are each independently an integer from 1 to 6; n and p are each independently 0 or 1; the sum of m and n and the sum of o and p is 6 or less; and $R^A$, $R^B$, $R^C$, $R^D$, $R^E$, $R^F$, $R^G$, and $R^H$ at each instance of m, n, o, and p are each independently hydrogen or $R^2$.

In some embodiments, $Y^1$ or $Y^{11}$ is $—(CR^AR^B)_m(CR^CR^D)_nC(O)OR^1$ or $—(CR^AR^B)_m(CR^CR^D)_nC(O)O(CR^GR^H)_p(CR^ER^F)_oC(O)OR^1$.

In certain embodiments, $Y^1$ or $Y^{11}$ is $—(CR^AR^B)_m(CR^CR^D)_nC(O)OR^1$.

In one embodiment, $R^A$, $R^B$, $R^E$, and $R^F$ at each instance of m and o are each independently hydrogen; and $R^C$, $R^D$, $R^G$, and $R^H$ at each instance of n and p are each independently hydrogen or $R^2$.

In one exemplary embodiment, $Y^1$ is $-(CH_2)_m(CR^C R^D)_nC(O)OR^1$, $-(CH_2)_m(CR^CR^D)_nOC(O)R^1$, $-(CH_2)_{m-1}C(O)O(CR^GR^H)_p(CH_2)_oC(O)OR^1$, or $-(CH_2)_{m-1}C(O)O(CH_2)_oOR^3$.

In another exemplary embodiment, $Y^{11}$ is $-(CH_2)_m(CR^CR^D)_nC(O)OR^1$, $-(CH_2)_m(CR^CR^D)_nOC(O)R^1$, $-(CH_2)_mC(O)O(CR^GR^H)_p(CH_2)_oC(O)OR^1$, or $-(CH_2)_nC(O)O(CH_2)_oOR^3$.

In another exemplary embodiment, $Y^1$ is $-(CH_2)_m(CR^CR^D)_nC(O)OR^1$ or $-(CH_2)_{m-1}C(O)O(CR^GR^H)_p(CH_2)_oC(O)OR^1$.

In another exemplary embodiment, $Y^{11}$ is $-(CH_2)_m(CR^CR^D)_nC(O)OR^1$ or $-(CH_2)_mC(O)O(CR^GR^H)_p(CH_2)_oC(O)OR^1$.

In one specifically contemplated embodiment, $Y^1$ is $-(CH_2)_mC(O)OR^1$ or $-(CH_2)_{m-1}C(O)O(CH_2)_oC(O)OR^1$.

In another specifically contemplated embodiment, $Y^{11}$ is $-(CH_2)_mC(O)OR^1$ or $-(CH_2)_mC(O)O(CH_2)_oC(O)OR^1$.

In another specifically contemplated embodiment, $Y^1$ or $Y^{11}$ is $-(CH_2)_mC(O)OR^1$.

In one exemplary embodiment, $Y^1$ is $-(CR^AR^B)_m(CR^CR^D)_nC(O)OR^1$, $-(CR^AR^B)_m(CR^CR^D)_nOC(O)R^1$, $-(CR^AR^B)_{m-1}(CR^CR^D)_nC(O)O(CR^GR^H)_p(CR^ER^F)_oC(O)OR^1$, or $-(CR^AR^B)_{m-1}(CR^CR^D)_nC(O)O(CR^GR^H)_p(CR^ER^F)_oOR^3$.

In one exemplary embodiment, $Y^{11}$ is $-(CR^AR^B)_m(CR^CR^D)_nC(O)OR^1$, $-(CR^AR^B)_m(CR^CR^D)_nOC(O)R^1$, $-(CR^AR^B)_m(CR^CR^D)_nC(O)OH$, $-(CR^AR^B)_m(CR^CR^D)_nC(O)O(CR^GR^H)_p(CR^ER^F)_oC(O)OR^1$, or $-(CR^AR^B)_m(CR^CR^D)_nC(O)O(CR^GR^H)_p(CR^ER^F)_oOR^3$.

In another exemplary embodiment, $Y^1$ is $-(CR^AR^B)_m(CR^CR^D)_nC(O)OR^1$ or $-(CR^AR^B)_{m-1}(CR^CR^D)_nC(O)O(CR^GR^H)_p(CR^ER^F)_oC(O)OR^1$; and $X^1$ and $X^2$ are each independently hydrogen, $R^2$, halo, $C_{1-6}$haloalkyl, $C_{1-6}$haloalkoxy, $SO_2R^{11}$, $OR^{11}$, or $C(O)R^{11}$ at any of the available 2-5 positions.

In another exemplary embodiment, $Y^{11}$ is $-(CR^AR^B)_m(CR^CR^D)_nC(O)OR^1$ or $-(CR^AR^B)_m(CR^CR^D)_nC(O)O(CR^GR^H)_p(CR^ER^F)_oC(O)OR^1$; and $X^1$ and $X^2$ are each independently hydrogen, $R^2$, halo, $C_{1-6}$haloalkyl, $C_{1-6}$haloalkoxy, $SO_2R^{11}$, $OR^{11}$, or $C(O)R^{11}$ at any of the available 2-5 positions.

In one specifically contemplated embodiment, $Y^1$ or $Y^{11}$ is $-(CR^AR^B)_m(CR^CR^D)_nC(O)OR^1$; and $X^1$ and $X^2$ are each independently hydrogen, $R^2$, halo, $C_{1-6}$haloalkyl, $C_{1-6}$haloalkoxy, $SO_2R^{11}$, or $OR^{11}$ at any of the available 2-5 positions.

In another specifically contemplated embodiment, $Y^1$ or $Y^{11}$ is $-(CR^AR^B)_m(CR^CR^D)_nC(O)OR^1$; $X^1$ and $X^2$ are each independently hydrogen, $R^2$, halo, $C_{1-6}$haloalkyl, $C_{1-6}$haloalkoxy, $SO_2R^{11}$, or $OR^{11}$ at any of the available 2-5 positions; and $Y^2$ is hydrogen or $C_{1-6}$alkyl.

In another specifically contemplated embodiment, $Y^1$ or $Y^{11}$ is $-(CR^AR^B)_m(CR^CR^D)_nC(O)OR^{11}$; $X^1$ and $X^2$ are each independently hydrogen, $R^2$, halo, $C_{1-6}$haloalkyl, $C_{1-6}$haloalkoxy, $SO_2R^{11}$, or $OR^{11}$ at any of the available 2-5 positions; and $Y^2$ is hydrogen or methyl.

In another specifically contemplated embodiment, $Y^1$ or $Y^{11}$ is $-(CR^AR^B)_m(CR^CR^D)_nC(O)OR^1$; $X^1$ and $X^2$ are each independently hydrogen, $R^2$, halo, $C_{1-6}$haloalkyl, $C_{1-6}$haloalkoxy, $SO_2R^{11}$, or $OR^{11}$ at any of the available 2-5 positions; and $Y^2$ is hydrogen.

In another specifically contemplated embodiment, $Y^1$ or $Y^{11}$ is $-(CR^AR^B)_m(CR^CR^D)_nC(O)OR^1$; $X^1$ and $X^2$ are each independently hydrogen, $R^2$, halo, $C_{1-6}$haloalkyl, $C_{1-6}$haloalkoxy, $SO_2R^{11}$, or $OR^1$ at any of the available 2-5 positions; $R^A$ and $R^B$ at each instance of m are hydrogen; and $Y^2$ is hydrogen or $C_{1-6}$alkyl.

In another specifically contemplated embodiment, $Y^1$ or $Y^{11}$ is $-(CR^AR^B)_m(CR^CR^D)_nC(O)OR^1$; $X^1$ and $X^2$ are each independently hydrogen, $R^2$, halo, $C_{1-6}$haloalkyl, $C_{1-6}$haloalkoxy, $SO_2R^{11}$, or $OR^1$ at any of the available 2-5 positions; $R^A$ and $R^B$ at each instance of m are hydrogen; and $Y^2$ is hydrogen or methyl.

In another specifically contemplated embodiment, $Y^1$ or $Y^{11}$ is $-(CR^AR^B)_m(CR^CR^D)_nC(O)OR^1$; $X^1$ and $X^2$ are each independently hydrogen, $R^2$, halo, $C_{1-6}$haloalkyl, $C_{1-6}$haloalkoxy, $SO_2R^{11}$, or $OR^{11}$ at any of the available 2-5 positions; $R^A$ and $R^B$ at each instance of m are hydrogen; and $Y^2$ is hydrogen.

In another specifically contemplated embodiment, $Y^1$ or $Y^{11}$ is $-(CR^AR^B)_m(CR^CR^D)_nC(O)OR^1$; $X^1$ is 2-chloro; $X^2$ is hydrogen, $R^2$, halo, $C_{1-6}$haloalkyl, $C_{1-6}$haloalkoxy, $SO_2R^{11}$, or $OR^{11}$ at any of the available 3-5 positions; $R^A$ and $R^B$ at each instance of m are hydrogen; and $Y^2$ is hydrogen or $C_{1-6}$alkyl.

In another specifically contemplated embodiment, $Y^1$ or $Y^{11}$ is $-(CR^AR^B)_m(CR^CR^D)_nC(O)OR$; $X^1$ is 2-chloro; $X^2$ is hydrogen, $R^2$, halo, $C_{1-6}$haloalkyl, $C_{1-6}$haloalkoxy, $SO_2R^{11}$, or $OR^{11}$ at any of the available 3-5 positions; $R^A$ and $R^B$ at each instance of m are hydrogen; and $Y^2$ is hydrogen or methyl.

In another specifically contemplated embodiment, $Y^1$ or $Y^{11}$ is $-(CR^AR^B)_m(CR^CR^D)_nC(O)OR$; $X^1$ is 2-chloro; $X^2$ is hydrogen, $R^2$, halo, $C_{1-6}$haloalkyl, $C_{1-6}$haloalkoxy, $SO_2R^{11}$, or $OR^{11}$ at any of the available 3-5 positions; $R^A$ and $R^B$ at each instance of m are hydrogen; and $Y^2$ is hydrogen.

In one embodiment, the compound of formula (I) is
3-((1-(2-chlorophenyl)-2-oxocyclohexyl)amino)propyl acetate,
ethyl 3-((1-(2-chlorophenyl)-2-oxocyclohexyl)amino)propanoate,
iso-propyl 3-((1-(2-chlorophenyl)-2-oxocyclohexyl)amino)propanoate,
n-propyl 3-((1-(2-chlorophenyl)-2-oxocyclohexyl)amino)propanoate,
ethyl 4-((1-(2-chlorophenyl)-2-oxocyclohexyl)amino)butanoate,
isopropyl 4-((1-(2-chlorophenyl)-2-oxocyclohexyl)amino)butanoate,
n-propyl 4-((1-(2-chlorophenyl)-2-oxocyclohexyl)amino)butanoate,
methyl 5-((1-(2-chlorophenyl)-2-oxocyclohexyl)amino)pentanoate,
ethyl 5-((1-(2-chlorophenyl)-2-oxocyclohexyl)amino)pentanoate,
isopropyl 5-((1-(2-chlorophenyl)-2-oxocyclohexyl)amino)pentanoate,
n-propyl 5-((1-(2-chlorophenyl)-2-oxocyclohexyl)amino)pentanoate,
ethyl 3-((1-(2-chlorophenyl)-2-oxocyclohexyl)(methyl)amino)propanoate,
ethyl 4-((1-(2-chlorophenyl)-2-oxocyclohexyl)(methyl)amino)butanoate, or
methyl 5-((1-(2-chlorophenyl)-2-oxocyclohexyl)(methyl)amino)pentanoate, or
a pharmaceutically acceptable salt or solvate thereof.

In one embodiment, the compound of formula (I) is
3-((1-(2-chlorophenyl)-2-oxocyclohexyl)amino)propyl acetate,
ethyl 3-((1-(2-chlorophenyl)-2-oxocyclohexyl)amino)propanoate, iso-propyl 3-((1-(2-chlorophenyl)-2-oxocyclohexyl)amino)propanoate,
n-propyl 3-((1-(2-chlorophenyl)-2-oxocyclohexyl)amino)propanoate,
ethyl 4-((1-(2-chlorophenyl)-2-oxocyclohexyl)amino)butanoate,
isopropyl 4-((1-(2-chlorophenyl)-2-oxocyclohexyl)amino)butanoate,
n-propyl 4-((1-(2-chlorophenyl)-2-oxocyclohexyl)amino)butanoate,
methyl 5-((1-(2-chlorophenyl)-2-oxocyclohexyl)amino)pentanoate,
ethyl 5-((1-(2-chlorophenyl)-2-oxocyclohexyl)amino)pentanoate,
isopropyl 5-((1-(2-chlorophenyl)-2-oxocyclohexyl)amino)pentanoate, or
n-propyl 5-((1-(2-chlorophenyl)-2-oxocyclohexyl)amino)pentanoate, or
a pharmaceutically acceptable salt or solvate thereof.

In another embodiment, the compound is
ethyl 3-((1-(2-chlorophenyl)-2-oxocyclohexyl)amino)propanoate,
iso-propyl 3-((1-(2-chlorophenyl)-2-oxocyclohexyl)amino)propanoate,
n-propyl 3-((1-(2-chlorophenyl)-2-oxocyclohexyl)amino)propanoate,
ethyl 4-((1-(2-chlorophenyl)-2-oxocyclohexyl)amino)butanoate,
isopropyl 4-((1-(2-chlorophenyl)-2-oxocyclohexyl)amino)butanoate,
n-propyl 4-((1-(2-chlorophenyl)-2-oxocyclohexyl)amino)butanoate,
methyl 5-((1-(2-chlorophenyl)-2-oxocyclohexyl)amino)pentanoate,
ethyl 5-((1-(2-chlorophenyl)-2-oxocyclohexyl)amino)pentanoate,
isopropyl 5-((1-(2-chlorophenyl)-2-oxocyclohexyl)amino)pentanoate,
n-propyl 5-((1-(2-chlorophenyl)-2-oxocyclohexyl)amino)pentanoate,
ethyl 3-((1-(2-chlorophenyl)-2-oxocyclohexyl)(methyl)amino)propanoate,
ethyl 4-((1-(2-chlorophenyl)-2-oxocyclohexyl)(methyl)amino)butanoate, or
methyl 5-((1-(2-chlorophenyl)-2-oxocyclohexyl)(methyl)amino)pentanoate, or
a pharmaceutically acceptable salt or solvate thereof.

In another embodiment, the compound is
ethyl 3-((1-(2-chlorophenyl)-2-oxocyclohexyl)amino)propanoate,
iso-propyl 3-((1-(2-chlorophenyl)-2-oxocyclohexyl)amino)propanoate,
n-propyl 3-((1-(2-chlorophenyl)-2-oxocyclohexyl)amino)propanoate,
ethyl 4-((1-(2-chlorophenyl)-2-oxocyclohexyl)amino)butanoate,
isopropyl 4-((1-(2-chlorophenyl)-2-oxocyclohexyl)amino)butanoate,
n-propyl 4-((1-(2-chlorophenyl)-2-oxocyclohexyl)amino)butanoate,
methyl 5-((1-(2-chlorophenyl)-2-oxocyclohexyl)amino)pentanoate,
ethyl 5-((1-(2-chlorophenyl)-2-oxocyclohexyl)amino)pentanoate,
isopropyl 5-((1-(2-chlorophenyl)-2-oxocyclohexyl)amino)pentanoate, or
n-propyl 5-((1-(2-chlorophenyl)-2-oxocyclohexyl)amino)pentanoate, or
a pharmaceutically acceptable salt or solvate thereof.

In one embodiment, the stereochemical configuration at position 2 of the cyclohexyl ring in the compound is (S).

In some embodiments, the compound comprises 95% or more of a single stereoisomer. In certain embodiments, the compound is stereoisomerically pure.

In one embodiment, the compound is a pharmaceutically acceptable salt. In one embodiment, the salt is a hydrochloride salt.

In one embodiment, the compound of formula (II) is a compound of formula (I) as defined in the first aspect or in any of the embodiments described above.

Asymmetric centers may exist in the compounds of formula (I) and (II). The asymmetric centers may be designated as (R) or (S), depending on the configuration of substituents in three dimensional space at the chiral carbon atom. All stereochemical isomeric forms of the compounds, including diastereomeric, enantiomeric, and epimeric forms, as well as d-isomers and l-isomers, and mixtures thereof, including enantiomerically enriched and diastereomerically enriched mixtures of stereochemical isomers, are included herein.

Individual enantiomers can be prepared synthetically from commercially available enantiopure starting materials or by preparing enantiomeric mixtures and resolving the mixture into individual enantiomers. Resolution methods include conversion of the enantiomeric mixture into a mixture of diastereomers and separation of the diastereomers by, for example, recrystallization or chromatography, and any other appropriate methods known in the art. Starting materials of defined stereochemistry may be commercially available or made and, if necessary, resolved by techniques well known in the art.

The compounds of formula (I) and (II) may also exist as conformational or geometric isomers, including cis, trans, syn, anti, entgegen (E), and zusammen (Z) isomers. All such isomers and any mixtures thereof are included herein.

Also included are any tautomeric isomers or mixtures thereof of the compounds. As would be appreciated by those skilled in the art, a wide variety of functional groups and other structures may exhibit tautomerism. Examples include, but are not limited to, keto/enol, imine/enamine, and thioketone/enethiol.

The compounds of formula (I) and (II) may also exist as isotopologues and isotopomers, wherein one or more atoms in the compounds are replaced with different isotopes. Suitable isotopes include, for example, $^1H$, $^2H$ (D), $^3H$ (T), $^{12}C$, $^{13}C$, $^{14}C$, $^{16}O$, and $^{18}O$. Procedures for incorporating such isotopes into the compounds described herein will be apparent to those skilled in the art. Isotopologues and isotopomers of the compounds are thus included herein.

Also included are pharmaceutically acceptable salts and solvates, including hydrates of the compounds. Such salts include, acid addition salts, base addition salts, and quaternary salts of basic nitrogen-containing groups. Acid addition salts can be prepared by reacting compounds, in free base form, with inorganic or organic acids. Examples of inorganic acids include, but are not limited to, hydrochloric, hydrobromic, hydroiodic, nitric, carbonic, sulfuric, and phosphoric acid. Examples of organic acids include, but are not limited to, lauric, acetic, trifluoroacetic, formic, propionic, succinic, glycolic, lactic, malic, tartaric, citric, ascorbic, maleic, fumaric, pyruvic, aspartic, glutamic, stearic, salicylic, mandelic, methanesulfonic, benzenesulfonic, isoethonic, sulfanilic, adipic, butyric, oxalic, and pivalic. Base addition salt can be prepared by reacting compounds, in free acid form, with inorganic or organic bases. Examples of inorganic base addition salts include alkali metal salts, alkaline earth metal salts, and other physiologically acceptable metal salts, for example, aluminium, calcium, lithium, magnesium, potassium, sodium, or zinc salts. Examples of organic base addition salts include amine salts, for example, salts of trimethylamine, diethylamine, ethanolamine, diethanolamine, and ethylenediamine. Quaternary salts of basic nitrogen-containing groups in the compounds may be may be prepared by, for example, reacting the compounds with alkyl halides such as methyl, ethyl, propyl, and butyl chlorides, bromides, and iodides, dialkyl sulfates such as dimethyl, diethyl, dibutyl, and diamyl sulfates, and the like.

The general chemical terms used in the formulae herein have their usual meaning.

The term "aliphatic" is intended to include saturated and unsaturated, nonaromatic, straight chain, branched, acyclic, and cyclic hydrocarbons. Those skilled in the art will appreciate that aliphatic groups include, for example, alkyl, alkenyl, alkynyl, cycloalkyl, and cycloalkenyl groups.

The term "alkyl" is intended to include straight chain and branched chain alkyl groups. In some embodiments, alkyl groups have from 1 to 12, from 1 to 10, from 1 to 8, from 1 to 6, or from 1 to 4 carbon atoms. Examples of straight chain alkyl groups include, but are not limited to, methyl, ethyl, n-propyl, n-butyl, n-pentyl, n-hexyl, n-heptyl, and n-octyl. Examples of branched alkyl groups include, but are not limited to, isopropyl, iso-butyl, sec-butyl, tert-butyl, neopentyl, isopentyl, and 2,2-dimethylpropyl.

The term "alkenyl" is intended to include straight and branched chain alkyl groups having at least one double bond between two carbon atoms. In some embodiments, alkenyl groups have from 2 to 12, from 2 to 10, from 2 to 8, from 2 to 6, or from 2 to 4 carbon atoms. In some embodiments, alkenyl groups have one, two, or three carbon-carbon double bonds. Examples of alkenyl groups include, but are not limited to, vinyl, allyl, —CH=CH($CH_3$), —CH=C($CH_3$)$_2$, —C($CH_3$)=CH$_2$, and —C($CH_3$)=CH($CH_3$).

The term "alkynyl" is intended to include straight and branched chain alkyl groups having at least one triple bond between two carbon atoms. In some embodiments, the alkynyl group have from 2 to 12, from 2 to 10, from 2 to 8, from 2 to 6, or from 2 to 4 carbon atoms. In some embodiments, alkynyl groups have one, two, or three carbon-carbon triple bonds. Examples include, but are not limited to, —C≡CH, —C≡CH$_3$, —CH$_2$C≡CH$_3$, and —C≡CH$_2$CH(CH$_2$CH$_3$)$_2$.

The term "cycloalkyl" is intended to include mono-, bi- or tricyclic alkyl groups. In some embodiments, cycloalkyl groups have from 3 to 12, from 3 to 10, from 3 to 8, from 3 to 6, from 3 to 5 carbon atoms in the ring(s). In some embodiments, cycloalkyl groups have 5 or 6 ring carbon atoms. Examples of monocyclic cycloalkyl groups include, but are not limited to, cyclopropyl, cyclobutyl, cyclopentyl, cyclohexyl, cycloheptyl, and cyclooctyl. In some embodiments, the cycloalkyl group has from 3 to 8, from 3 to 7, from 3 to 6, from 4 to 6, from 3 to 5, or from 4 to 5 ring carbon atoms. Bi- and tricyclic ring systems include bridged, spiro, and fused cycloalkyl ring systems. Examples of bi- and tricyclic ring cycloalkyl systems include, but are not limited to, bicyclo[2.1.1]hexanyl, bicyclo[2.2.1]heptanyl, adamantyl, and decalinyl.

The term "cycloalkenyl" is intended to include non-aromatic cycloalkyl groups having at least one double bond between two carbon atoms. In some embodiments, cycloalkenyl groups have one, two or three double bonds. In some embodiments, cycloalkenyl groups have from 4 to 14, from 5 to 14, from 5 to 10, from 5 to 8, or from 5 to 6 carbon atoms in the ring(s). In some embodiments, cycloalkenyl groups have 5, 6, 7, or 8 ring carbon atoms. Examples of cycloalkenyl groups include cyclohexenyl, cyclopentenyl, cyclohexadienyl, butadienyl, pentadienyl, and hexadienyl.

The term "aryl" is intended to include cyclic aromatic hydrocarbon groups that do not contain any ring heteroatoms. Aryl groups include monocyclic, bicyclic and tricyclic ring systems. Examples of aryl groups include, but are not limited to, phenyl, azulenyl, heptalenyl, biphenyl, fluorenyl, phenanthrenyl, anthracenyl, indenyl, indanyl, pentalenyl, and naphthyl. In some embodiments, aryl groups have from 6-14, from 6 to 12, or from 6-10 carbon atoms in the ring(s). In some embodiments, the aryl groups are phenyl or naphthyl. Aryl groups include aromatic-aliphatic fused ring systems. Examples include, but are not limited to, indanyl and tetrahydronaphthyl.

The term "heterocyclyl" is intended to include non-aromatic ring systems containing 3 or more ring atoms, of which one or more is a heteroatom. In some embodiments, the heteroatom is nitrogen, oxygen, or sulfur. In some embodiments, the heterocyclyl group contains one, two, three, or four heteroatoms. In some embodiments, heterocyclyl groups include mono-, bi- and tricyclic rings having from 3 to 16, from 3 to 14, from 3 to 12, from 3 to 10, from 3 to 8, or from 3 to 6 ring atoms. Heterocyclyl groups include partially unsaturated and saturated ring systems, for example, imidazolinyl and imidazolidinyl. Heterocyclyl groups include fused and bridged ring systems containing a heteroatom, for example, quinuclidyl. Heterocyclyl groups include, but are not limited to, aziridinyl, azetidinyl, azepanyl, diazepanyl, 1,3-dioxanyl, 1,3-dioxolanyl, isoxazolidinyl, morpholinyl, piperazinyl, piperidinyl, pyranyl, pyrazolidinyl, pyrrolinyl, pyrrolidinyl, tetrahydrofuranyl, tetrahydrothienyl, thiadiazolidinyl, and trithianyl.

The term "heteroaryl" is intended to include aromatic ring systems containing 5 or more ring atoms, of which, one or more is a heteroatom. In some embodiments, the heteroatom is nitrogen, oxygen, or sulfur. In some embodiments, heteroaryl groups include mono-, bi- and tricyclic ring systems having from 5 to 16, from 5 to 14, from 5 to 12, from 5 to 10, from 5 to 8, or from 5 to 6 ring atoms. Heteroaryl groups include, but are not limited to, pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, pyrazolopyridinyl, triazolopyridinyl, benzotriazolyl, benzoxazolyl, benzothiazolyl, imidazopyridinyl, isoxazolopyridinylxanthinyl, guaninyl, quinolinyl, isoquinolinyl, tetrahydroquinolinyl, quinoxalinyl, and quinazolinyl. Heteroaryl groups include fused ring systems in which all of the rings are aromatic, for example, indolyl, and fused ring systems in which only one of the rings is aromatic, for example, 2,3-dihydroindolyl.

The term "halo" or "halogen" is intended to include F, Cl, Br, and I.

As used herein, the term "substituted" is intended to mean that one or more hydrogen atoms in the group indicated is replaced with one or more independently selected suitable substituents, provided that the normal valency of each atom to which the substituent/s are attached is not exceeded, and that the substitution results in a stable compound.

As used herein, the term "and/or" means "and", or "or", or both.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9, and 10) and also any range of rational numbers within that range (for example, 2 to 8, 1.5 to 5.5, and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Although the present invention is broadly as defined above, those persons skilled in the art will appreciate that the invention is not limited thereto and that the invention also includes embodiments of which the following description gives examples.

BRIEF DESCRIPTION OF THE DRAWINGS

The invention will now be described with reference to the Figures in which.

DETAILED DESCRIPTION OF THE INVENTION

Figure 1A:
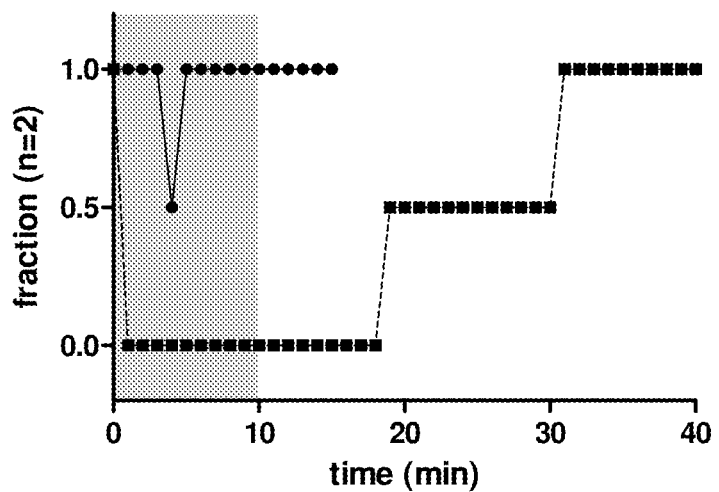
FIG. 1A and FIG. 1B are graphs showing time-course for anaesthesia (loss and recovery of righting reflex) with ketamine and rac-C2nPr (FIG. 1A) and rac-C4Me (FIG. 1B). The grey panel shows the duration of drug infusion (measurement taken every minute). ••••: test compound. ■■■■ ketamine.

The present invention generally relates to ketamine derivatives and their use as anaesthetics, analgesics, or sedatives.

The applicants have invented new ketamine derivatives of the formula (I) as defined above which can provide anaesthetic and/or analgesic effects similar to ketamine, but at least in some embodiments have the advantage of shortening the period of recovery after administration of the derivative has ceased.

The applicants have also found that certain known ketamine derivatives, which are encompassed by the formula (II), can surprisingly be used as anaesthetics and have advantageous properties similar to those of the compounds of formula (I).

Compounds of formula (I) or (II) may be prepared using methods of synthesis known in the art or methods analogous thereto.

In one embodiment, the method comprises reacting a compound of the formula (III):

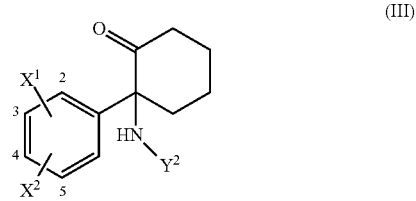

(III)

wherein $Y^2$, $X^1$, and $X^2$ are as defined above with an alkylating agent of the formula $Y^1$—Z or $Y^{11}$—Z, wherein Z is a suitable leaving group and $Y^1$ and $Y^{11}$ are as defined above, to provide the compound of the formula (I) or (II), respectively.

In one embodiment, Z is halo.

In some embodiments, the reaction is carried out in the presence of a base. In certain embodiments, the reaction is carried out in the presence of an inorganic base, for example, a carbonate base.

In some embodiments, the reaction is carried out in the presence of a suitable solvent, for example, an aprotic solvent.

The reaction may be carried out at any suitable temperature. In some embodiments, the reaction is carried out in the presence of a suitable solvent at reflux. In other embodiments, the reaction is carried out at ambient temperature.

In some embodiments, the compound of formula (III) is prepared by a method comprising heating a compound of the formula (IV)

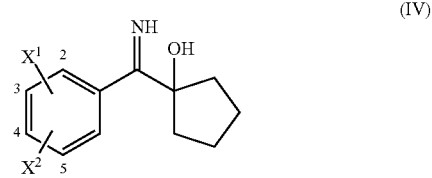

(IV)

wherein $X^1$ and $X^2$ are as defined above in a suitable liquid reaction medium to provide a compound of the formula (III), wherein $Y^2$ is hydrogen.

In some embodiments, the method comprises heating the compound of the formula (IV) in a suitable solvent. In certain embodiments, the compound is heated at a temperature of 75, 100, 125, 150, 175, or 200° C. or more.

In some embodiments, the compound of formula (IV) is prepared by a method comprising reacting a compound of the formula (V)

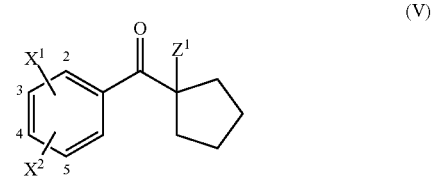

(V)

wherein $X^1$ and $X^2$ are as defined above and $Z^1$ is halo with $NH_3/NH_4OH$.

In some embodiments, the compound of formula (V) is prepared by a method comprising reacting a compound of the formula (VI)

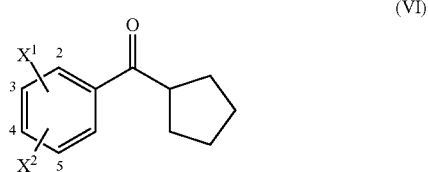

(VI)

wherein $X^1$ and $X^2$ are as defined above with a halogenating agent.

In one embodiment, the halogenating agent is copper (II) bromide.

In some embodiments, the reaction is carried out in a suitable solvent.

Schemes 1 to 4 below illustrate the preparation of certain compounds of formula (I) and (II) wherein $X^1$ is chloro and $X^2$ is hydrogen from (2-o-chlorophenyl)-2-amino-cyclohexanone (norketamine).

(S)-Norketamine (S-24) is synthesized following a reported procedure [Hong & Davisson. *J. Pharm. Sci.*, 1982, 71, 912].

Commercially available (2-chlorophenyl)(cyclopentyl) methanone (31) is brominated by refluxing with $CuBr_2$ in EtOAc. The brominated intermediate (22) is converted to the corresponding imino cyclopentanol (23) by stirring in $NH_4OH$ solution saturated with $NH_3$ gas. Thermal rearrangement of the hydrochloride salt of imino cyclopentanol in Dowtherm A at 200° C. affords racemic norketamine (rac-24).

The (S)-enantiomer of norketamine (S-24) is obtained by resolution with L-(R,R)-(+)-tartaric acid. The (R)- enantiomer of norketamine (R-24) may be obtained in an analogous fashion from D-(S,S)-(−)-tartaric acid.

Compounds of formula (I) or (II) are synthesized by treatment of racemic or (S)-norketamine with alkyl halides corresponding to $Y^1$. Enantiopure (R)-norketamine and non-racemic enantiomeric mixtures of norketamine may be also used.

The compounds may be converted to hydrochloride salts using HCl gas.

Scheme 2.

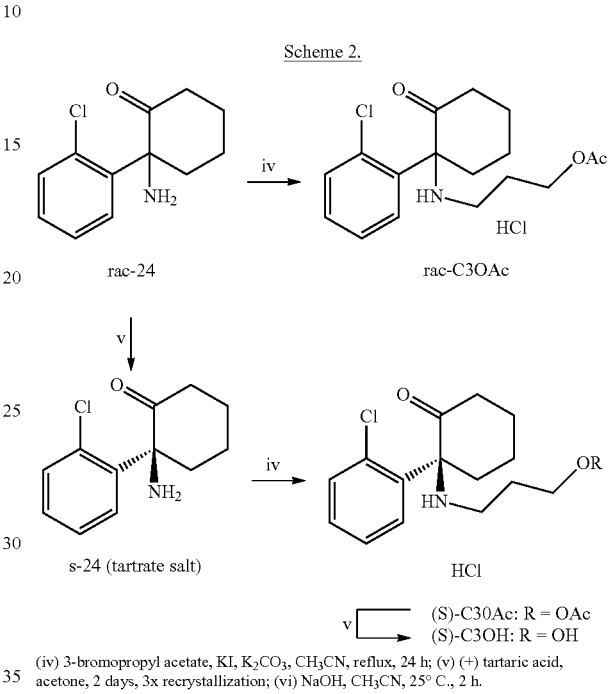

(iv) 3-bromopropyl acetate, KI, $K_2CO_3$, $CH_3CN$, reflux, 24 h; (v) (+) tartaric acid, acetone, 2 days, 3x recrystallization; (vi) NaOH, $CH_3CN$, 25° C., 2 h.

Scheme 1

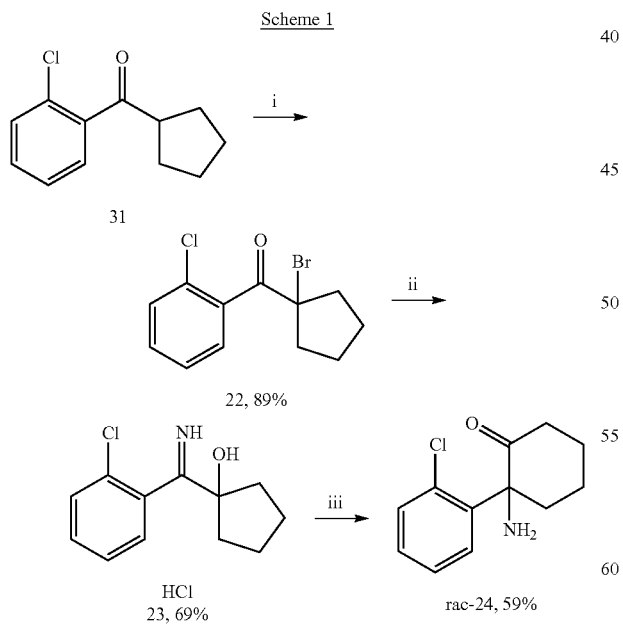

(i) $CuBr_2$, EtOAc, reflux, 3 h; (ii) (a) $NH_3/NH_4OH$, 25° C., 5 days, (b) HCl(g), isopropanol/diethyl ether, 0° C., 3 h; (iii) Dowtherm A, 200° C., 12 min.

Scheme 3 rac-24 or S-24

X = Me, Et, $^iPr$, $^nPr$
n = 2, 3, 4

Alkyl halides corresponding to $Y^1$ are commercially available or may be prepared by methods known in the art or analogous thereto.

Compounds wherein $Y^2$ is $R^2$ may be prepared from compounds of formula (I) or (II) wherein $Y^2$ is hydrogen by treatment with an alkylating agent corresponding to $R^2$. Such compounds may also be prepared by reductive amination with an aldehyde (e.g. formaldehyde when $R^2$ is methyl) or ketone corresponding to $R^2$.

Scheme 4.

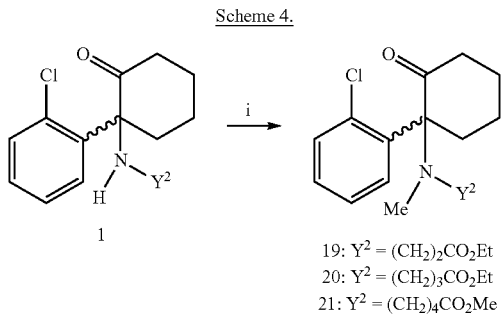

19: $Y^2 = (CH_2)_2CO_2Et$
20: $Y^2 = (CH_2)_3CO_2Et$
21: $Y^2 = (CH_2)_4CO_2Me$ (i) NaCNBH$_3$, HCHO, AcOH, MeOH, 25° C., 24 h.

Compounds of formula (I) and (II) wherein the phenyl ring is substituted with different $X^1$ and $X^2$ may be prepared by, for example, using suitably substituted (phenyl)(cyclopentyl)methanones.

Certain compounds of formula (II) and methods for their preparation are described in WO 2004/045601.

Preparation of the compounds may involve the protection and deprotection of various chemical groups. The need for protection and deprotection, and the selection of appropriate protecting groups, can be readily determined by a person skilled in the art. Protecting groups and methods for protection and deprotection are well known in the art [see e.g. T. W. Greene and P. G. M. Wuts, *Protective Groups in Organic Synthesis*, 3$^{rd}$ Ed., Wiley & Sons, Inc., New York (1999)].

The compounds of formula (I) and (II) have analgesic, anaesthetic, and/or sedative activity and are therefore useful for treating pain and/or anaesthetizing and/or sedating subjects.

The term "treatment", and related terms such as "treating" and "treat", as used herein, in the context of treating pain, relates generally to treatment, of a human or a non-human subject, in which some desired therapeutic effect is achieved. The therapeutic effect may, for example, be inhibition, reduction, amelioration, halt, or prevention of the pain.

Analgesia is the alleviation or elimination of the sensation of pain. As used herein the term "pain" encompasses a wide range of clinical manifestations, and it has a broad meaning. Pain perception is highly subjective, and different people experience pain in different ways and with greatly different intensities. The International Association for the Study of Pain defines pain as an unpleasant sensory and emotional experience associated with actual or potential tissue damage, or described in terms of such damage. Non-limiting types and causes of pain include neuralgia, myalgia, hyperalgesia, hyperpathia, neuritis, and neuropathy. Pain may also be caused by physical trauma, such as burns or surgery. In one embodiment, the pain is pain resistant to treatment with opioids.

The term "anaesthetize" and related terms such as "anaesthetizing" as used herein means to induce a loss of sensation and usually of consciousness without loss of vital functions artificially produced by the administration of one or more agents that block responses of the body to painful stimuli, for example the absence of a response to a surgical incision.

The term "sedate" and related terms such as "sedating" as used herein means to induce a state of depressed consciousness in which a patient or subject retains the ability to independently and continuously maintain an open airway and a regular breathing pattern, and to respond appropriately and rationally to physical stimulation and verbal commands. Sedation may be evaluated using, for example, the Ramsay Sedation Scale.

The methods of the present invention comprise administering compounds of formula (I) or (II) to a subject.

The subject may be a human or non-human animal. Non-human animals include, for example, production animals, such as, cattle, sheep, swine, deer, and goats; companion animals, such as, dogs, cats, and horses; zoo animals, such as, zebras, elephants, giraffes, and large cats; research animals, such as, mice, rats, rabbits, and guinea pigs; furbearing animals, such as, mink; birds, such as, ostriches, emus, hens, geese, turkeys, and ducks; fresh- and salt-water fish, such as, trout, salmon, carp, and eels; and reptiles, such as lizards and snakes. In one embodiment, the subject is a human.

The methods comprise administering a therapeutically effective amount of the compound to the subject. A "therapeutically effective amount" of a compound is an amount effective to demonstrate a desired therapeutic effect either alone or in combination with other agents.

The therapeutically effective amount of the compound to be administered to a subject depends on, for example, the purpose for which the compound is administered, mode of administration, nature and dosage of any co-administered compounds, and characteristics of the subject, such as general health, other diseases, age, sex, genotype, body weight and tolerance to drugs. A person skilled in the art will be able to determine appropriate dosages having regard to these any other relevant factors.

In one embodiment, the dose of administered is from about 0.01 mg per kg of body weight (0.01 mg/kg) to about 100 mg/kg.

The compounds may be administered by any suitable route. The route may depend on the therapeutic purpose for which the compound is administered.

In one exemplary embodiment, the compound is administered intravenously.

In one specifically contemplated embodiment, the compound is administered by intravenous bolus. In another specifically contemplated embodiment, the compound is administered intravenously by continuous infusion.

In certain embodiments, the compound is administered as an intravenous bolus and by intravenous infusion. In one embodiment, the compound is administered as an intravenous bolus and by continuous intravenous infusion.

In some embodiments, the compound is administered as an intravenous bolus at a dose from about 0.01 mg per kg of body weight (0.01 mg/kg) to about 100 mg/kg.

In some embodiments, the compound is administered by continuous intravenous infusion at a dose from about 0.1 mg/kg/min to about 10 mg/kg/min.

In one specifically contemplated embodiment, the compound is administered for anesthesia as an intravenous bolus at a dose from about 0.01 mg per kg of body weight (0.01 mg/kg) to about 100 mg/kg and as a continuous intravenous infusion at a dose from about 0.1 mg/kg/min to about 10 mg/kg/min. Smaller doses would be used for sedation and analgesia.

The compounds of formula (I) and (II) are generally prepared in a formulation or pharmaceutical composition appropriate for administration by a particular route. Examples of administration route include transdermal, transmucosal (e.g. nasal, transbuccal, sublingual, vaginal, and rectal), oral, pulmonary (i.e. inhalation), and parenteral (e.g. intravenous, intraarterial, intraperitoneal, intradermal, intramuscular, intraventricular, or subcutaneous).

The formulations generally comprise a pharmaceutically acceptable diluent, excipient, or carrier. Any suitable diluent, excipient, or carrier can be used provided that it is non-toxic and compatible with the other ingredients of the composition. The diluent, excipient, or carrier used depends on the intended route of administration.

The formulation or pharmaceutical composition may be manufactured by any method known in the art, for example, by conventional mixing, dissolving, granulating, levigating, emulsifying, encapsulating, entrapping, or compression. Numerous diluents, excipients, and carriers and methods for preparing pharmaceutical compositions are known in the art [see e.g. Remington's Pharmaceutical Sciences, Mack Publishing Co., (2000)].

Suitable formulations for administering the compounds include, for example, tablets, capsules, suppositories, solutions, and powders etc.

The content of the pharmaceutically active compound(s) is typically in the range from 0.05 to 90 wt.-% of the composition as a whole. In one embodiment, the content is from 0.1 to 50 wt.-% of the composition as a whole.

Suitable compositions include for example tablets, capsules, suppositories, solutions and powders etc. Tablets may comprise a solid carrier or diluent. Liquid pharmaceutical compositions may comprise a liquid carrier, for example, water, petroleum, animal or vegetable oils, mineral oil or synthetic oil. Liquid compositions may also comprise physiological saline solution, dextrose or other carbohydrate solution, glycols e.g. ethylene glycol, propylene glycol or polyethylene glycol, etc. Capsules may comprise a solid carrier e.g. gelatin. Such formulations will be well known to a person skilled in the art.

The pharmaceutical composition may be formulated for intravenous, cutaneous or subcutaneous injection. The active ingredient is generally in the form of a parenterally acceptable aqueous solution, which is pyrogen-free and has a suitable pH, isotonicity and stability. Those skilled in the art will be able to prepare suitable solutions. The solutions may comprise isotonic vehicles e.g. sodium chloride injection, Ringer's injection, etc. Preservatives, stabilisers, buffers antioxidants and/or other suitable additives may be included as required.

The composition of the present invention comprises a compound of formula (I) or a pharmaceutically acceptable salt or solvate thereof, and a pharmaceutically acceptable diluent, excipient, or carrier. The composition may be formulated as described above.

The formulations may comprise or be used or administered in combination, for example sequentially or simultaneously, with one or more additional therapeutic agents, for example alpha-2 adrenergic drugs such as clonidine or dexmedetomidine.

In one embodiment, the composition further comprises a buffer, stabiliser, or adjuvant.

The uses of the present invention involve the manufacture of medicaments. The medicaments are also formulated as described above.

EXAMPLES

The following non-limiting examples are provided to illustrate the present invention and in no way limit the scope thereof.

The structures and physicochemical properties of selected compounds representative of the invention are given in Table 1.

Lipophilicities (c log P) were calculated using ChemBioDraw v12.02 (CambridgeSoft, UK). pKa values were calculated using ACD/PhysChem Suite v12 (ACD/Labs, Toronto, Canada).

TABLE 1

Details of representative compounds (I)

| Compd. | $X^1$ | $X^2$ | $Y^1$ | $Y^2$ | Form | Purity (%)[a] | clogP[b] | pKa[c] |
|---|---|---|---|---|---|---|---|---|
| rac-C3OAc | 2-Cl | H | $(CH_2)_3OAc$ | H | R/S | 97.2 | 2.86 | 6.20 |
| (S)-C3OAc | 2-Cl | H | $(CH_2)_3OAc$ | H | S | 95.8 | 2.86 | 6.20 |
| rac-C2Et | 2-Cl | H | $(CH_2)_2CO_2Et$ | H | R/S | 97.2 | 3.05 | 4.35 |
| (S)-C2Et | 2-Cl | H | $(CH_2)_2CO_2Et$ | H | S | 99.1 | 3.39 | 4.35 |
| rac-C2iPr | 2-Cl | H | $(CH_2)_2CO_2{}^iPr$ | H | R/S | 99.0 | 3.36 | 4.35 |
| (S)-C2iPr | 2-Cl | H | $(CH_2)_2CO_2{}^iPr$ | H | S | 99.5 | 3.36 | 4.35 |
| (R)-C2iPr | 2-Cl | H | $(CH_2)_2CO_2{}^iPr$ | H | R | 99.5 | 3.36 | 4.35 |
| rac-C2nPr | 2-Cl | H | $(CH_2)_2CO_2{}^nPr$ | H | R/S | 99.0 | 3.58 | 4.35 |
| rac-C3Et | 2-Cl | H | $(CH_2)_3CO_2Et$ | H | R/S | 95.3 | 3.39 | 5.86 |
| rac-C3iPr | 2-Cl | H | $(CH_2)_3CO_2{}^iPr$ | H | R/S | 98.4 | 3.70 | 5.86 |
| rac-C3nPr | 2-Cl | H | $(CH_2)_3CO_2{}^nPr$ | H | R/S | 97.2 | 3.92 | 5.85 |
| rac-C4Me | 2-Cl | H | $(CH_2)_4CO_2Me$ | H | R/S | 99.1 | 2.77 | 6.29 |
| (S)-C4Me | 2-Cl | H | $(CH_2)_4CO_2Me$ | H | S | 97.0 | 2.77 | 6.29 |
| rac-C4Et | 2-Cl | H | $(CH_2)_4CO_2Et$ | H | S | 94.4 | 3.29 | 6.29 |
| rac-C4iPr | 2-Cl | H | $(CH_2)_4CO_2{}^iPr$ | H | R/S | 97.6 | 3.60 | 6.29 |
| rac-C4nPr | 2-Cl | H | $(CH_2)_4CO_2{}^nPr$ | H | R/S | 95.4 | 3.82 | 6.29 |
| 19 | 2-Cl | H | $(CH_2)_2CO_2Et$ | Me | R/S | 93.0 | 3.69 | 4.77 |
| 20 | 2-Cl | H | $(CH_2)_3CO_2Et$ | Me | R/S | 94.0 | 3.48 | 5.51 |
| 21 | 2-Cl | H | $(CH_2)_4CO_2Me$ | Me | R/S | 94.8 | 3.32 | 5.74 |

[a]Purity by reverse-phase HPLC;
[b]ClogP calculated using ChemBioDraw Ultra v12.02;
[c]pKa calculated using ACD/PhysChem Suite v12.
Ketamine has a measured (Volgyi, G. et al. Anal. Chim. Acta 2007, 583, 418-428) aqueous pKa of 7.49 and a calculated clogP of 2.22. The closest match to this were the acetates (rac-C3OAc and (S)-C3OAc). Next closest in physicochemical properties were the C4 methyl esters (rac-C4Me and (S)-C4Me). The esters overall showed a range of both pKa values (from 4.35 to 6.29) and lipophilicities (from 2.77 to 3.92).

General Details

All reagents and solvents were obtained from commercial suppliers and used without further purification unless otherwise stated. Reactions requiring anhydrous conditions were performed under nitrogen atmospheres. Reactions were monitored by thin layer chromatography (TLC) on preloaded silica gel F254 plates (Sigma-Aldrich) with a UV indicator. Column chromatography was performed with Merck 230-400 mesh silica gel. $^1H$ and $^{13}C$ NMR spectra were obtained with a Bruker Avance 400 spectrometer at 400 MHz for 1H and 100 MHz for $^{13}C$ spectra. Spectra were obtained in $CDCl_3$ or $(CD_3)_2SO$. The chemical shifts are reported in parts per million (δ) downfield using tetramethylsilane ($SiMe_4$) as internal standard. Spin multiplicities are given as s (singlet), d (doublet), dd (double doublet), br (broad), m (multiplet), and q (quartet). Coupling constants (J values) were measured in hertz (Hz). All LC/MS data were gathered by direct injection of methanolic solutions into a Surveyor MSQ mass spectrometer using an atmospheric pressure chemical ionization (APCI) with a corona voltage of 50 V and a source temperature of 400° C. Final products were analyzed by reverse-phase HPLC (Alltima C18 5 μm column, 150 mm×3.2 mm; Alltech Associated, Inc., Deerfield, Ill.) using an Agilent HP1100 equipped with a diode array detector. The mobile phase was 80% $CH_3CN/20\%$ H₂O (v/v) in 45 mM HCO₂NH₄ at pH 3.5 and 0.5 mL/min. The purity was determined by monitoring at 272 nm and was ≥95% for final products unless otherwise stated. The enantiomeric purity was analyzed by chiral HPLC (Chiralcel OJ-H column, 0.46 cm×45 cm). The mobile phase was 85% hexanes/15% EtOH with a flow rate of 0.6 mL/min. The purity was determined by monitoring at 254 and 280 nm and was ≥95% unless otherwise stated. The final product purity was also assessed by combustion analysis carried out in the Campbell Micro analytical Laboratory, University of Otago (Dunedin, New Zealand). Melting points were determined on an Electrothermal 2300 Melting Point Apparatus and are uncorrected. DCM refers to dichloromethane, DMF refers to N,N-dimethylformamide, EtOAc refers to ethyl acetate, EtOH refers to ethanol.

Example 1

Rac-3-((1-(2-Chlorophenyl)-2-oxocyclohexyl) amino)propyl Acetate Hydrochloride (rac-C3OAc). (Scheme 2)

(2-chlorophenyl)(cyclopentyl)methanone [US 20080268071] (21) (10 g, 48.0 mmol) was dissolved in ethyl acetate (100 mL) followed by addition of Cu(II)Br₂ (27 g, 120.9 mmol). The solution was refluxed for 2.5 h and cooled to 25° C. The solid was filtered and the filtrate was evaporated under reduced pressure. Some solid began to form while evaporating solvent under reduced pressure. DCM (100 mL) was added to the solid formed and solution cooled to 0° C. in an ice bath. After standing for 10 min. the solution was filtered and the filtrate concentrated under reduced pressure to obtain (1-bromocyclopentyl)(2-chlorophenyl) methanone (22) as a yellow oil (12.3 g, 89%). $^1$H NMR (400 MHz, CDCl₃) δ 7.70 (dd, J=7.4, 1.8 Hz, 1H), 7.43 (dd, J=7.9, 1.3 Hz), 7.37 (td, J=7.4, 1.8 Hz, 1H), 7.30 (td, J=7.4, 1.3 Hz, 1H), 2.45-2.27 (m, 4H), 2.09-2.01 (m, 2H), 1.89-1.82 (m, 2H); $^{13}$C NMR (101 MHz, CDCl₃) δ 199.47, 138.87, 130.83, 130.55, 130.16, 128.33, 126.49, 74.29, 40.42, 23.26. MS m/z 289.3 (M2H⁺, 24%) 207.4 (M-Br⁻, 100%)

Ammonium hydroxide (200 mL) was cooled to 0° C. in an ice bath and was saturated with NH₃ gas for 5 min. The solution was added to a flask containing 22 (12.74 g, 44.5 mmol) and stirred vigorously at 25° C. for 5 days. The brown clumps formed were separated from the solvent and resuspended in hexanes (150 mL). After stirring in hexanes for 4 h, the precipitate formed was filtered and dried to obtain 23 (8.15 g, 81%) as a pale yellow solid. This was suspended in 8 mL of 2-propanol and cooled to 0° C. in an ice bath. HCl gas was bubbled through the solution for 2 min. and diethyl ether (16 mL) was added. Upon standing at 0° C. for 3 h a pale yellow precipitate was formed which was filtered, dried under vacuum to obtain 1-((2-chlorophenyl) (imino)methyl)cyclopentanol hydrochloride (23-HCl) [Parcell, R. F. & Sanchez, J. P. J. Org. Chem. 1981, 46, 5055]. (7.21 g). $^1$H NMR (400 MHz, CDCl₃) δ 14.05 (br, 1H), 12.28 (br, 1H), 7.61-7.32 (m, 4H), 2.23 (br, 2H), 1.98 (m, 4H), 1.69 (br, 2H); $^{13}$C NMR (101 MHz, CDCl₃) δ 195.76, 132.74, 131.42, 130.57, 128.99, 128.85, 126.82, 85.56, 39.47, 38.78, 24.46, 23.85. MS m/z 224.4 (MH⁺).

To Dowtherm A (142 mL) heated to 200° C. was added in portions 23 (18 g, 69.2 mmol). The heating was continued for 12 min. and cooled to 0° C. in an ice bath. The reaction mixture along with precipitate formed was poured into diethyl ether (500 mL) and allowed to stand overnight. The white precipitate formed was filtered and washed with diethyl ether (100 mL). The precipitate was dissolved in water (200 mL) and neutralized with 2 N NaOH. The water layer was extracted with DCM (3×100 mL), dried over Na₂SO4 and solvent evaporated. The residue obtained was purified by passing through a short silica gel column eluting with DCM (100%) to 10% MeOH/DCM to give racemic 2-amino-2-(2-chlorophenyl)cyclohexanone (norketamine) (rac-24) [Parcell, R. F. & Sanchez, J. P. J. Org. Chem. 1981, 46, 5055] (9.2 g, 59%). $^1$H NMR (400 MHz, CDCl₃) δ 7.69 (dd, J=7.8, 1.7 Hz 1H), 7.39-7.33 (m, 2H), 7.26 (td, J=7.6, 1.6 Hz, 1H), 2.79-2.72 (m, 1H), 2.63-2.56 (m, 1H), 2.51-2.43 (m, 1H), 2.08-2.0 (m, 1H), 1.88 (br, 1H), 1.81-1.75 (m, 2H), 1.72-1.63 (m, 1H).

A solution of rac-24 (200 mg, 0.89 mmol), 3-bromopropyl acetate [Demko, Z. P. & Sharpless K. B. Org. Lett. 2001, 3, 4091] (194 mg, 1.07 mmol), KI (45 mg, 0.27 mmol), K₂CO₃ (371 mg, 2.7 mmol) was dissolved in CH₃CN (5 mL). The reaction mixture was heated to reflux for 24 h. After completion of reaction the reaction mixture was cooled to room temperature and solvent evaporated under reduced pressure. The residue was purified by column chromatography on silica gel eluting with hexanes (100%), EtOAc/hexanes (40%). The solvent was evaporated under reduced pressure to obtain the desired product as yellow oil (173 mg, 59%). The yellow oil was dissolved in diethyl ether (5 mL) and was cooled to 0° C. in an ice bath. Dry HCl gas was bubbled through the solution at 0° C. for 2 min. The solvent was evaporated under reduced pressure to obtain a yellow solid. The yellow solid was dissolved in EtOAc (1 mL) and sonicated at 25° C. for 2 min. The white precipitate formed was diluted with EtOAc (5 mL) and filtered, washed with EtOAc and dried under vacuum to give rac-C3OAc.HCl (107 mg, 33%), mp 180-183° C. $^1$H NMR (400 MHz, CDCl₃) δ 11.71 (br, 1H), 8.19 (d, J=7.6 Hz, 1H), 8.09 (br, 1H), 7.58 (m, 1H), 7.46 (d, J=4.0 Hz, 2H), 4.15 (m, 1H), 4.08 (m, 1H), 3.81 (dm, J=12.0 Hz, 1H), 3.19 (br, 1H), 2.74 (d, J=12.0 Hz, 1H), 2.68-2.60 (m, 2H), 2.47 (br, 1H), 2.28 (t, J=14 Hz, 1H), 2.12 (br, 2H), 2.09 (s, 3H), 1.84 (br, 2H), 1.54 (br, 1H); $^{13}$C NMR (101 MHz, CDCl₃) δ 206.20, 171.04, 135.14, 132.56, 132.34, 131.79, 129.16, 128.92, 77.49, 62.22, 41.87, 40.63, 40.01, 29.91, 25.84, 21.82, 21.02. MS m/z 324.2 (MH⁺). MS m/z 324.2 (MH⁺). Anal. calcd for C₁₇H₂₃Cl₂NO₃: C, 56.67; H, 6.43; N, 3.89; Cl, 19.68. Found: C, 56.49; H, 6.61; N, 3.69.

Example 2

(S)-3-((1-(2-Chlorophenyl)-2-oxocyclohexyl)amino) propyl Acetate Hydrochloride [(S)-C3OAc] (Scheme 2)

Resolution of norketamine was achieved by following a published procedure [Hong & Davisson. J. Pharm. Sci., 1982, 71, 912]. A solution of rac-24 (13.2 g, 59.1 mmol) in MeOH (33 mL) was treated with L-(R,R)-(+)-tartaric acid (8.9 g, 59.1 mmol) in MeOH (118 mL). The reaction mixture was stirred overnight at 25° C. and filtered to remove any solid impurities. The filtrate was evaporated and the white solid obtained washed with 2-butanone (264 mL). The white solid was suspended in acetone (1750 mL) and heated to reflux until most of the solid was dissolved. The solution was cooled to room temperature and allowed to stand for 2 days. The crystals formed were filtered and recrystallized two additional times in acetone (1750 mL and 800 mL respectively) to obtain (S)-2-amino-2-(2-chlorophenyl)cyclohexanone, (S)-norketamine [(S)-24] as the tartrate salt. $^1$H NMR (400 MHz, DMSO-d₆) δ 7.85 (d, J=7.8 Hz), 7.39 (t, J=7.4 Hz, 2H), 7.34 (d, J=7.5 Hz, 1H), 4.21 (s, 2H), 2.78-2.70 (m, 1H), 2.32 (dt, J=15.1, 4.4 Hz, 1H), 1.96-1.81 (m, 3H), 1.73-1.60 (m, 2H), one proton submerged with DMSO-$d_6$ peak; $^{13}$C NMR (101 MHz, DMSO-$d_6$) δ 208.6, 173.320, 131.96, 130.28, 129.1 (2), 128.93, 127.09, 71.93, 64.84, 38.31, 37.5, 25.79, 20.84. MS m/z 224.2 (MH$^+$). Mp: 190-191° C.

The (S)-norketamine tartrate salt was dissolved in water (200 mL) and neutralized with 2 N NaOH. The aqueous layer was extracted with DCM (3×100 mL). The combined DCM layer was washed with brine (100 mL) and dried over Na$_2$SO$_4$. Evaporation of solvent under reduced pressure afforded (S)-norketamine free base [(S)-24] (4.96 g) as a pale yellow viscous oil. $^1$H NMR (400 MHz, CDCl$_3$) δ 7.70 (dd, J=7.8, 1.7 Hz), 7.38-7.31 (m, 2H), 7.28-7.23 (m, 1H), 2.79-2.71 (m, 1H), 2.63-2.56 (m, 1H), 2.51-2.43 (m, 1H), 2.08-2.02 (m, 1H), 1.89-1.74 (m, 3H), 1.71-1.63 (m, 1H); $^{13}$C NMR (101 MHz, CDCl$_3$) δ 212.75, 140.49, 133.02, 131.0, 128.97, 128.32, 127.20, 66.42, 41.25, 38.98, 28.32, 22.16. MS m/z 224.2 (MH$^+$).

A solution of (S)-24 (1 g, 4.47 mmol), 3-bromopropyl acetate [Demko, Z. P. & Sharpless K. B. *Org. Lett.* 2001, 3, 4091] (971 mg, 5.36 mmol), KI (223 mg, 1.34 mmol), K$_2$CO$_3$ (1.85 g, 13.4 mmol) was dissolved in CH$_3$CN (12 mL). The reaction mixture was heated to reflux for 24 h. After completion of reaction the reaction mixture was cooled to room temperature and solvent evaporated under reduced pressure. The residue was purified by column chromatography on silica gel eluting with hexanes (100%), EtOAc/hexanes (40%). The solvent was evaporated under reduced pressure to obtain the desired product as yellow oil (695 mg, 48%). The yellow oil was dissolved in diethyl ether (20 mL) and was cooled to 0° C. in an ice bath. Dry HCl gas was bubbled through the solution at 0° C. for 2 min. The white precipitate formed was filtered and resuspended in EtOAc (20 mL) and stirred for 10 min at room temperature. The white precipitate was filtered to give (S)-C3OAc hydrochloride (512 mg, 29%), mp 169-172° C. $^1$H NMR (400 MHz, CDCl$_3$) δ 11.87 (br, 1H), 8.20 (d, J=8.2 Hz, 1H), 7.62-7.54 (m, 1H), 7.48 (d, J=3.8 Hz, 2H), 7.39 (br, 1H), 4.12 (q, J=7.1 Hz, 2H), 3.83 (dm, J=14.4 Hz, 1H), 3.11-3.02 (m, 1H), 2.75 (d, J=12.5 Hz, 1H), 2.70-2.61 (m, 1H), 2.51 (br, 1H), 2.32 (t, J=7.3 Hz, 2H), 2.24 (t, J=11.1 Hz, 1H), 2.05 (br, 1H), 1.99-1.88 (m, 2H), 1.83 (d, J=14.5 Hz, 2H), 1.76-1.61 (m, 3H), 1.24 (t, J=7.1 Hz, 3H); $^{13}$C NMR (101 MHz, CDCl$_3$) δ 205.41, 173.07, 135.21, 132.58, 132.06, 131.67, 128.99, 73.20, 60.57, 43.59, 40.82, 39.62, 33.65, 29.68, 26.07, 22.27, 21.77, 14.31. MS m/z 352.2 (MH$^+$). Anal. calcd for C$_{19}$H$_{27}$Cl$_2$NO$_3$: C, 58.77; H, 7.01; N, 3.61; Cl, 18.26. Found: C, 58.81; H, 7.1, N, 3.51; Cl, 18.31.

General Procedure for Synthesis of N-Alkylated Norketamine Esters (Scheme 3)

A solution of rac-24 or (S)-24 (1 eq.), the appropriate alkyl halide (1.2 eq. or 6 eq. in case of ethyl-3-bromo propionate), KI (0.3 eq.) and K$_2$CO$_3$ (3 eq.) was dissolved in CH$_3$CN (4.5 mL/mmol). The solution was heated to 80° C. in a sealed tube for 24 h (72 h in case of ethyl-3-bromo propionate). The reaction mixture was cooled to room temperature and solvent evaporated. The residue was purified by column chromatography on silica gel eluting with hexanes (100%), EtOAc/hexanes (20-35%). The solvent was evaporated under reduced pressure to obtain the desired product as yellow oil. This was dissolved in diethyl ether (5 mL) and was cooled to 0° C. in an ice bath. Dry HCl gas was bubbled through the solution at 0° C. for 2 min. The solvent was evaporated under reduced pressure to obtain a yellow solid. The yellow solid was dissolved in EtOAc (2 mL) and sonicated at 25° C. for 2 min. The white precipitate formed was diluted with EtOAc (10 mL) and filtered, washed with EtOAc and dried under vacuum to obtain the product as hydrochloride salt.

The following compounds were prepared according to this general procedure.

Example 3

Ethyl 3-((1-(2-chlorophenyl)-2-oxocyclohexyl) amino)propanoate Hydrochloride (rac-C2Et)

From rac-24 and ethyl 3-bromopropionate (33% yield), mp 199-202° C. $^1$H NMR (400 MHz, CDCl$_3$) δ 12.24 (br, 1H, NH$_2$), 8.13 (d, J=8.0 Hz, 2H, ArH, NH$_2$), 7.61-7.54 (m, 1H, ArH), 7.49 (d, J=3.8 Hz, 2H,), 4.23 (q, J=7.2 Hz, 2H), 3.78 (dm, J=14.3 Hz, 1H), 3.59-3.45 (m, 1H), 3.25 (q, J=5.4 Hz, 1H), 2.73 (br, 2H), 2.68-2.54 (m, 2H), 2.23 (td, J=13.7, 2.5 Hz, 1H), 2.14-2.02 (m, 1H), 1.89-1.82 (m, 2H), 1.65-1.59 (m, 1H), 1.28 (t, J=7.2 Hz, 3H, CH$_2$C$\underline{H}_3$); $^{13}$C NMR (101 MHz, CDCl$_3$) δ 206.10, 171.94, 135.27, 132.57, 132.40, 131.85, 129.05, 128.57, 73.42, 61.67, 40.30, 39.71, 39.63, 30.38, 29.93, 21.86, 14.18; MS m/z 324.2 (MH$^+$). Anal. calcd for C$_{17}$H$_{23}$Cl$_2$NO$_3$: C, 56.67; H, 6.43; N, 3.89; Cl, 19.68. Found: C, 56.65; H, 6.57; N, 3.89; Cl, 19.90.

Example 3A (S)-Ethyl 3-((1-(2-chlorophenyl)-2-oxocyclohexyl) amino) propanoate Hydrochloride [(S)-C2Et]

From (S)-24 and ethyl 3-bromopropanoate (54%), mp 208-210° C. $^1$H NMR (400 MHz, CDCl$_3$) δ 12.08 (br, 1H), 8.25 (br, 1H), 8.13 (d, J=8.0 Hz, 1H), 7.61-7.56 (m, 1H), 7.49 (br, 2H), 4.21 (q, J=7.2 Hz, 2H), 3.76 (dm, J=14.3, 3.2 Hz, 1H), 3.55-3.46 (m, 1H), 3.28 (q, J=9.97 Hz, 1H), 2.75-2.56 (m, 4H), 2.26 (td, J=14.14 Hz, 1H), 2.08 (br, 1H), 1.90-1.78 (m, 2H), 1.61 (br, 1H), 1.28 (t, J=7.2 Hz, 3H); $^{13}$C NMR (101 MHz, CDCl$_3$) δ 206.35, 172.38, 135.08, 132.39, 132.33, 131.71, 128.91, 128.27, 73.32, 61.75, 40.08, 39.57, 29.91, 29.89, 21.69, 14.02 (IC overlapping). MS m/z 324.2 (MH$^+$). HRMS calculated for C$_{17}$H$_{23}$ClNO$_3$ (MH$^+$) 324.1361, found 324.1370.

Example 4

Iso-Propyl 3-((1-(2-chlorophenyl)-2-oxocyclohexyl) amino)propanoate Hydrochloride (rac-C2iPr)

From rac-24 and isopropyl 3-bromopropanoate (48%), mp 203-205° C. $^1$H NMR (400 MHz, CDCl$_3$) δ 12.0 (br, 1H), 8.27 (br, 1H), 8.14 (d, J=8.0 Hz, 1H), 7.61-7.55 (m, 1H), 7.49 (br, 2H), 5.13-5.04 (m, 1H), 3.79 (dm, J=14.3 Hz, 1H), 3.52-3.44 (m, 1H), 3.28 (br, 1H), 2.74 (br, 2H), 2.65-2.56 (m, 2H), 2.24 (td, J=13.8, 3.2 Hz, 1H), 2.07 (br, 1H), 1.89-1.78 (m, 2H), 1.65-1.62 (m, 1H), 1.26 (d, J=5.01 Hz, 6H); $^{13}$C NMR (101 MHz, CDCl$_3$) δ 206.57, 172.2, 135.23, 132.63, 132.49, 131.84, 129.07, 129.03, 73.51, 69.86, 40.23, 39.85, 30.27, 30.08, 21.93, 21.84. MS m/z 338.2 (MH$^+$). HRMS calculated 338.1517, found 338.1529.

Example 4A (S)-Isopropyl 3-((1-(2-chlorophenyl)-2-oxocyclohexyl)amino)propanoate hydrochloride [(S)-C2iPr]

From (S)-24 and isopropyl 3-bromopropanoate (29%), mp 208-211° C. $^1$H NMR (400 MHz, CDCl$_3$) δ 12.22 (br, 1H), 8.14 (dbr, J=8.1 Hz, 2H), 7.61-7.55 (m, 1H), 7.49 (br, 2H), 5.12-5.06 (m, 1H), 3.79 (dm, J=14.4 Hz, 1H), 3.52-3.43 (m, 1H), 3.26 (q, J=11.9 Hz, 1H), 2.71 (br, 2H), 2.67-2.55 (m, 2H), 2.21 (td, J=14.1, 3.3 Hz, 1H), 2.07 (br, 1H), 1.89-1.78 (m, 2H), 1.63 (br, 1H), 1.27 (app. dd, J=4.93, 1.25 Hz, 6H); $^{13}$C NMR (101 MHz, CDCl$_3$) δ 206.62, 172.23, 135.24, 132.62, 132.48, 131.84, 129.08, 128.42, 73.48, 69.86, 40.24, 39.87, 30.28, 30.09, 21.93, 21.87, 21.84. MS m/z 338.2 (MH$^+$). HRMS calculated for C$_{18}$H$_{25}$ClNO$_3$ (MH$^+$) 338.1517, found 338.1524.

Example 4B (R)-Isopropyl 3-((1-(2-chlorophenyl)-2-oxocyclohexyl)amino)propanoate Hydrochloride [(R)-C2iPr]

From (R)-24 and isopropyl 3-bromopropanoate (29%), mp 216-219° C. $^1$H NMR (400 MHz, CDCl$_3$) δ 12.20 (br, 1H), 8.14 (dbr, J=8.1 Hz, 2H), 7.60-7.56 (m, 1H), 7.49 (br, 2H), 5.14-5.04 (m, 1H), 3.80 (dm, J=13.6 Hz, 1H), 3.51-3.44 (m, 1H), 3.26 (br, 1H), 2.73 (br, 2H), 2.64-2.56 (m, 2H), 2.21 (t, J=13.2 Hz, 1H), 2.06 (br, 1H), 1.89-1.79 (m, 2H), 1.64 (br, 1H), 1.26 (app. dd, J=4.81, 1.40 Hz, 6H); $^{13}$C NMR (101 MHz, CDCl$_3$) δ 206.71, 172.36, 135.23, 132.67, 132.51, 131.85, 129.11, 128.39, 73.5, 69.94, 40.24, 39.95, 30.26, 30.13, 21.95, 21.89, 21.85. MS m/z (MH$^+$). HRMS calculated for C$_{18}$H$_{25}$ClNO$_3$ (MH$^{+)}$ 338.1517, found 338.1521.

(R)-24 was prepared by a procedure analogous to that described above for the preparation of (S)-24 using D-(S,S)-(−)-tartaric acid, rather than L-(R,R)-(+)-tartaric acid.

Example 5

N-Propyl 3-((1-(2-chlorophenyl)-2-oxocyclohexyl)amino)propanoate Hydrochloride (rac-C2nPr)

From rac-24 and propyl 3-bromopropanoate (44%) mp 163-165° C. $^1$H NMR (400 MHz, CDCl$_3$) δ 11.68 (br, 1H), 8.69 (br, 1H), 8.14 (d, J=8.0 Hz, 1H), 7.61-7.54 (m, 1H), 7.49 (br, 2H), 4.07 (t, J=6.8 Hz, 2H), 3.74 (dm, J=14.3 Hz, 1H), 3.53-3.43 (m, 1H), 3.38 (br, 1H), 2.81-2.71 (m, 3H), 2.64-2.57 (m, 1H), 2.35 (td, J=13.8, 3.2 Hz, 1H), 2.07 (br, 1H), 1.92-1.80 (m, 2H), 1.68-1.54 (m, 3H), 0.92 (t, J=7.4 Hz, 3H); $^{13}$C NMR (101 MHz, CDCl$_3$) δ 206.03, 172.0, 135.28, 132.48, 132.37, 131.84, 128.99, 128.6, 73.4, 67.22, 40.31, 39.57, 30.28, 29.9, 21.9, 21.81, 10.42. MS m/z 338.2 (MH$^+$). HRMS calculated 338.1517, found 338.1526.

Example 6

Ethyl 4-((1-(2-chlorophenyl)-2-oxocyclohexyl)amino)butanoate Hydrochloride (rac-C3Et)

From rac-24 and ethyl 4-bromobutanoate (37% yield), mp 186-189° C. $^1$H NMR (400 MHz, CDCl$_3$) δ 11.14 (br, 1H, NH$_2$), 9.14 (br, 1H, NH$_2$), 8.26 (d, J=8.1 Hz, 1H), 7.62-7.49 (m, 1H), 7.45 (d, J=3.8 Hz, 2H), 4.11 (q, J=7.1 Hz, 2H), 3.75 (dm, J=14.4 Hz, 1H), 3.38-3.26 (m, 1H), 2.75-2.64 (m, 1H), 2.64-2.58 (m, 1H), 2.43-2.26 (m, 2H), 2.45-2.28 (m, 2H), 2.14-2.07 (m, 1H), 1.98 (br, 2H), 1-91-1.79 (m, 1H), 1.58-1.44 (m, 1H), 1.23 (t, J=7.1 Hz, 3H); $^{13}$C NMR (101 MHz, CDCl$_3$) δ 206.03, 173.16, 135.11, 132.76, 132.08, 131.61, 129.19, 129.02, 73.17, 61.04, 43.54, 40.86, 40.00, 32.24, 29.72, 21.64, 14.27. MS m/z 338.2 (MH$^+$). Anal. calcd for C$_{18}$H$_{25}$Cl$_2$NO$_3$: C, 57.76; H, 6.73; N, 3.74; Cl, 18.94. Found: C, 57.55; H, 6.92; N, 3.64; Cl, 18.73.

Example 7

Isopropyl 4-((1-(2-chlorophenyl)-2-oxocyclohexyl)amino)butanoate hydrochloride (rac-C3iPr)

From rac-24 and isopropyl 4-bromobutanoate [Fox, M. E., et al. J. Org. Chem. 2005, 70, 1227] (24% yield), mp 167-169° C. $^1$H NMR (400 MHz, CDCl$_3$) δ 11.41 (br, 1H), 8.94 (br, 1H), 8.26 (d, J=8.1 Hz, 1H), 7.68-7.50 (m, 1H), 7.45 (d, J=3.9 Hz, 2H), 4.99 (m, 1H), 3.79 (dm, J=14.4 Hz, 1H), 3.31-3.21 (m, 1H), 2.75-2.68 (m, 1H), 2.66-2.59 (m, 2H), 2.58-2.49 (m, 1H), 2.42-2.48 (m, 1H), 2.34 (t, J=10.8 Hz, 2H), 2.11-1.98 (m, 2H), 1.84 (d, J=10.2 Hz, 2H), 1.58-1.46 (m, 1H), 1.22 (dd, J=6.28, 2.2 Hz, 6H); $^{13}$C NMR (101 MHz, CDCl$_3$) δ 206.29, 173.46, 135.04, 132.84, 132.13, 131.62, 129.08, 129.06, 73.11, 68.81, 43.70, 40.84, 40.21, 32.79, 29.90, 21.91, 21.68. MS m/z 352.2 (MH$^+$). Anal. calcd for C$_{19}$H$_{27}$Cl$_2$NO$_3$: C, 58.77; H, 7.01; N, 3.61. Found: C, 58.57; H, 7.2; N, 3.54.

Example 8

N-Propyl 4-((1-(2-chlorophenyl)-2-oxocyclohexyl)amino)butanoate Hydrochloride (rac-C3nPr)

From rac-24 and n-propyl 4-bromobutanoate (19%), mp 160-161° C. $^1$H NMR (400 MHz, CDCl$_3$) δ 11.10 (br, 1H), 9.23 (br, 1H), 8.27 (d, J=8.1 Hz, 1H), 7.59-7.52 (m, 1H), 7.44 (d, J=5.1 Hz, 2H), 4.01 (t, J=6.8 Hz, 2H), 3.76 (dm, J=14.4 Hz, 1H), 3.39-3.28 (m, 1H), 2.70 (t, J=7.8 Hz, 1H), 2.66 (t, J=6.9 Hz, 1H), 2.62-2.54 (m, 1H), 2.51 (td, J=7.0, 2.8 Hz, 2H), 2.47-2.41 (m, 1H), 2.39-2.30 (m, 1H), 2.15-2.06 (m, 1H), 2.0 (br, 1H), 1.85 (td, J=8.0, 3.9 Hz, 2H), 1.57-1.66 (m, 2H), 1.50 (q, J=14.4 Hz, 1H), 0.91 (t, J=7.4 Hz, 3H); $^{13}$C NMR (101 MHz, CDCl$_3$) δ 205.92, 173.47, 135.12, 132.78, 132.05, 131.59, 129.23, 129.0, 73.16, 66.62, 43.54, 40.86, 39.99, 32.19, 29.77, 22.0, 21.78, 21.70, 10.48. MS m/z 352.2 (MH$^+$).

Example 9

Rac-Methyl 5-((1-(2-chlorophenyl)-2-oxocyclohexyl)amino)pentanoate Hydrochloride (rac-C4Me)

From rac-24 and ethyl 5-bromopentanoate, followed by purification by preparative HPLC (41%). $^1$H NMR (400 MHz, CDCl$_3$) δ 7.53 (dd, J=7.8, 1.6 Hz, 1H), 7.36 (dd, J=7.8, 1.4 Hz, 1H), 7.31 (dt, J=7.8, 7.6, 1.5 Hz, 1H), 7.25-7.21 (m, 1H), 3.64 (s, 3H), 2.77-2.69 (m, 1H), 2.55-2.42 (m, 2H), 2.36-2.30 (m. 1H), 2.26 (t, J=7.4H, 2H), 2.09-1.73 (m, 7H), 1.66-1.58 (m, 2H), 1.55-1.40 (m, 2H). HPLC 99%.

Example 10

(S)-Methyl 5-((1-(2-chlorophenyl)-2-oxocyclohexyl)amino)pentanoate Hydrochloride [(S)-C4Me]

From (S)-24 and ethyl 5-bromopentanoate (42%), mp (MeOH/EtOAc) 188-191° C., $^1$H NMR (400 MHz, CDCl$_3$)

δ 7.52 (dd, J=7.82, 1.68 Hz, 1H), 7.36 (dd, J=7.8, 1.4 Hz, 1H), 7.31 (dt, J=7.8, 7.60, 1.45 Hz, 1H), 7.23 (dt, J=8.0; 1.7 Hz, 1H), 3.65 (s, 3H), 2.76-2.68 (m, 1H), 2.55-2.42 (m, 2H), 2.36-2.30 (m, 1H), 2.26 (t, J=7.4 Hz, 2H), 2.08-1.74 (m, 7H), 1.66-1.58 (M, 2H), 1.57-1.37 (m, 3H), Analysis Calc. for $C_{18}H_{25}C_{12}NO_3$: C, 57.8; H, 6.7; Cl, 18.9, N, 3.7; found C, 57.7, H, 6.8 Cl, 18.9N, 3.7.

Example 11

Rac-Ethyl 5-((1-(2-chlorophenyl)-2-oxocyclohexyl)amino)pentanoate hydrochloride (rac-C4Et)

From rac-24 and ethyl 5-bromopentanoate (29%), mp 169-172° C. $^1$H NMR (400 MHz, CDCl$_3$) δ 11.87 (br, 1H), 8.20 (d, J=8.2 Hz, 1H), 7.62-7.54 (m, 1H), 7.48 (d, J=3.8 Hz, 2H), 7.39 (br, 1H), 4.12 (q, J=7.1 Hz, 2H), 3.83 (dm, J=14.4 Hz, 1H), 3.11-3.02 (m, 1H), 2.75 (d, J=12.5 Hz, 1H), 2.70-2.61 (m, 1H), 2.51 (br, 1H), 2.32 (t, J=7.3 Hz, 2H), 2.24 (t, J=11.1 Hz, 1H), 2.05 (br, 1H), 1.99-1.88 (m, 2H), 1.83 (d, J=14.5 Hz, 2H), 1.76-1.61 (m, 3H), 1.24 (t, J=7.1 Hz, 3H); $^{13}$C NMR (101 MHz, CDCl$_3$) δ 205.41, 173.07, 135.21, 132.58, 132.06, 131.67, 129.34, 128.99, 73.20, 60.57, 43.59, 40.82, 39.62, 33.65, 29.68, 26.07, 22.27, 21.77, 14.31. MS m/z 352.2 (MH$^+$). Anal. calcd for $C_{19}H_{27}Cl_2NO_3$: C, 58.77; H, 7.01; N, 3.61; Cl, 18.26. Found: C, 58.81; H, 7.1, N, 3.51; Cl, 18.31.

Example 12

Isopropyl 5-((1-(2-chlorophenyl)-2-oxocyclohexyl)amino)pentanoate Hydrochloride (rac-C4iPr)

From rac-24 and isopropyl 5-bromovalerate (40%), mp 161-163° C. $^1$H NMR (400 MHz, CDCl$_3$) δ 11.04 (br, 1H), 8.78 (br, 1H), 8.24 (d, J=8.0 Hz, 1H), 7.59-7.53 (m, 1H), 7.47 (br, 2H), 5.01-4.92 (m, 1H), 3.74 (dm, J=14.4 Hz, 1H), 3.29-3.21 (m, 1H), 2.73 (d, J=12.2 Hz, 1H), 2.64 (td, J=13.3 Hz, 6.3, 1H), 2.54-2.42 (m, 2H), 2.26-2.21 (m, 2H), 2.10-1.99 (m, 2H), 1.94-1.83 (m, 2H), 1.78 (d, J=17.6 Hz, 1H), 1.71-1.47 (m, 3H), 1.20 (dd, J=6.3, 1.2 Hz, 6H); $^{13}$C NMR (101 MHz, CDCl$_3$) δ 205.7, 172.68, 135.18, 132.61, 132.13, 131.72, 129.26, 129.04, 73.25, 67.95, 43.66, 40.80, 39.76, 33.95, 29.78, 26.12, 22.25, 21.97, 21.8. MS m/z 366.2 (MH$^+$). HRMS calculated 366.1830, found 366.1842.

Example 13

N-Propyl 5-((1-(2-chlorophenyl)-2-oxocyclohexyl)amino)pentanoate Hydrochloride (rac-C4nPr)

From rac-24 and propyl 5-bromopentanoate (45%), $^1$H NMR (400 MHz, CDCl$_3$) δ 11.23 (br, 1H), 8.49 (br, 1H), 8.23 (d, J=8.0 Hz, 1H), 7.59-7.52 (m, 1H), 7.46 (br, 2H), 4.0 (t, J=6.8 Hz, 2H), 3.76 (dm, J=14.3 Hz, 1H), 3.24-3.18 (m, 1H), 2.74 (br, 1H), 2.69-2.61 (m, 1H), 2.46 (t, J=14.0 Hz, 2H), 2.29 (td, J=7.5, 2.9 Hz, 2H), 2.04-1.95 (m, 1H), 1.92-1.89 (m, 1H), 1.87-1.83 (m, 1H), 1.79 (dbr, J=15.3 Hz, 1H), 1.73-1.57 (m, 5H), 1.54-1.47 (m, 1H), 0.91 (t, J=7.4 Hz, 3H); $^{13}$C NMR (101 MHz, CDCl$_3$) δ 205.98, 173.29, 135.14, 132.6, 132.19, 131.74, 129.17, 129.08, 73.28, 66.31, 43.68, 40.77, 39.88, 33.58, 29.85, 26.16, 22.16, 22.06, 21.81, 10.5. MS m/z 366.2 (MH$^+$). HRMS calculated 366.1830, found 366.1839.

General Procedure for Reductive Methylation of N-Alkylated Norketamine Esters (Scheme 4)

Norketamine ester (0.9 mmol) was dissolved in MeOH (20 mL) and cooled to 0° C. in an ice bath. Acetic acid (0.2 mL, 3.6 mmol) and NaCNBH$_3$ (112 mg, 1.8 mmol) was added to the above solution and stirred at 0° C. for 5 min. Formaldehyde (37% in H$_2$O, 2.2 mmol) was added at 0° C. and reaction mixture allowed to stir at 25° C. for 24 h. The reaction mixture was quenched with NaHCO$_3$ and diluted with water. The aqueous layer was extracted with CH$_2$Cl$_2$ (3×20 mL), washed with brine and dried over Na$_2$SO$_4$. The solvent was evaporated under reduced pressure to obtain the product as yellow oil. The yellow oil was dissolved in Et$_2$O (5 mL), cooled to 0° C. in an ice bath and treated with HCl gas for 1 min. Solvent was evaporated and the residue was resuspended in EtOAc (2 mL) and sonicated. The precipitate formed was diluted with EtOAc (10 mL) and filtered, dried to give the product as the HCl salt.

Example 14

Ethyl 3-((1-(2-chlorophenyl)-2-oxocyclohexyl)(methyl)amino)propanoate (19)

From reductive methylation of rac-C2Et, (97%). $^1$H NMR (400 MHz, CDCl$_3$) δ 7.38 (dd, J=7.8, 1.4 Hz, 1H), 7.36-7.33 (m, 1H), 7.30 (td, J=7.9, 1.4 Hz, 1H), 7.25-7.21 (m, 1H), 4.10 (q, J=7.2 Hz, 2H), 3.11-3.04 (m, 1H), 2.97-2.90 (m, 1H), 2.80-2.73 (m, 1H), 2.58 (t, J=6.7 Hz, 2H), 2.49-2.45 (m, 2H), 2.43 (s, 3H), 2.05-1.91 (m, 2H), 1.89-1.72 (m, 2H), 1.65-1.56 (m, 1H), 1.24 (t, J=7.2 Hz, 3H); $^{13}$C NMR (101 MHz, CDCl$_3$) δ 208.1, 172.7, 138.0, 134.07, 131.68, 129.86, 18.64, 126.65, 74.58, 60.37, 47.76, 41.19, 36.97, 36.14, 34.73, 27.28, 22.33, 14.27. MS m/z 338.5 (MH$^+$). HRMS calculated for $C_{18}H_{25}ClNO_3$ (MH$^+$) 338.1517, found 338.1514.

Example 15

Ethyl 4-((1-(2-chlorophenyl)-2-oxocyclohexyl)(methyl)amino)butanoate Hydrochloride (20)

From reductive methylation of rac-C3Et (97%). Mixture of rotamers. $^1$H NMR (400 MHz, CDCl$_3$) δ 11.97 (br, 1H), 11.79 (br, 1H), 8.46 (d, J=8.0 Hz, 1H), 7.93 (d, J=7.6 Hz, 1H), 7.64-7.46 (m, 6H), 4.12-4.04 (m, 4H), 3.96 (t, J=9.3 Hz, 1H), 3.69 (d, J=14.8 Hz, 1H), 3.47 (1H), 3.25 (d, J=14.5 Hz, 1H), 3.16 (s, 3H), 2.78 (br, 6H), 2.69-2.55 (m, 5H), 2.48-2.34 (m, 3H), 2.14 (br, 3H), 1.97 (br, 3H), 1.84 (br, 5), 1.48-1.39 (m, 2H), 1.31-1.19 (m, 6H); $^{13}$C NMR (101 MHz, CDCl$_3$) δ 205.26, 204.28, 172, 136.05, 135.91, 133.57, 132.87, 132.77, 132.65, 132.55, 132.11, 129.2, 128.53, 127.69, 60.85, 53.32, 52.16, 42.65, 41.99, 37.37, 37.17, 36.59, 35.39, 31.49, 29.16, 22.22, 22.13, 20.64, 20.55, 14.3 (some C not seen for both rotamers). MS m/z 352.2 (MH$^+$). HRMS calculated for $C_{19}H_{27}ClNO_3$ (MH$^+$) 352.1674, found 352.1687.

Example 16

Methyl 5-((1-(2-chlorophenyl)-2-oxocyclohexyl)(methyl)amino)pentanoate (21)

From reductive methylation of rac-C4Me, (97%). $^1$H NMR (400 MHz, CDCl$_3$) δ 7.41 (d, J=7.5 Hz, 2H), 7.38-7.29 (m, 2H), 3.66 (s, 3H), 2.83 (br, 2H), 2.61-2.57 (m, 3H), 2.49 (br, 3H), 2.30 (t, J=7.1 Hz, 2H), 2.10-1.94 (m, 3H), 1.88-1.77 (m, 3H), 1.62-1.59 (m, 3H); $^{13}$C NMR (101 MHz, CDCl$_3$) δ 206.75, 173.94, 134.77, 133.19, 132.01, 131.14, 130.12, 127.44, 52.02, 51.62, 41.63, 37.0, 35.86, 33.66, 28.04, 27.07, 22.58, 22.27 (IC overlapping). MS m/z 352.2

(MH+). HRMS calculated HRMS calculated for $C_{19}H_{27}ClNO_3$ (MH+) 352.1674, found 352.1683.

Biological Activity

All animal experiments were conducted at the Ruakura Research Centre, Hamilton, New Zealand, using experimental protocols reviewed and approved by the Ruakura Animal Ethics Committee (ethics ref 12604).

Following acquisition of baseline physiologic parameters (heart rate, respiratory rate, PWR, and righting reflex (RR)) adult female Sprague-Dawley rats of approximately 350-450 g were put under non-traumatic restraint and the marginal vein of the tail was cannulated. Ketamine or a compound of the invention at 10 mg/ml was administered via a minibore extension tube adequately secured to the tail. Infusions were commenced at a rate (weight-adjusted) to deliver 20 mg/kg/min initially (until the pedal withdrawal reflex score PWR=1), then were reduced to a rate of 6.7 mg/kg/min. Infusion rate was then titrated in an up-and-down fashion to maintain dorsal recumbency and a PWR=1 to 10 minutes before cessation. Three rats were used in each study, with each group of rats also acting as their own ketamine control. The order of study drug administration was determined by prior odds/evens randomisation with a recovery interval of at least one hour afforded between experiments. PWR and RR were recorded at 1 minute intervals throughout. The times from cessation of infusion to return of righting reflex (RRR), and from cessation of infusion to the animals displaying independent locomotion (walk) were recorded.

The results are provided in Tables 2 and 3 below.

Pedal Withdrawal Reflex (PWR) Scoring:

Nociceptive testing in animals was conducted via 1 second application of constant pressure (firm digital pressure) over the forepaw of the animal. Pedal withdrawal reflex testing is primarily used to assess analgesic effect, and responses are graded accordingly: 0, absent; 1, flicker; 2, moderate withdrawal; 3, fast withdrawal; 4, Fast withdrawal with cry/preceding apnoea (modified from Buitrago, S. et al. *J. Amer. Assoc. Lab. Animal. Sci.* 2008, 47, 11-17).

Loss of Righting Reflex (LRR):

This is primarily used to assess anaesthetic hypnotic effect. Righting reflex is judged absent when the rat fails to right from a position of dorsal recumbency to a position of sternal recumbency on three attempts performed in rapid succession. Dose to LRR is termed effective potency.

TABLE 2

Anaesthetic effects of ketamine and compounds of the invention in a rat infusion study

| Compd | LRR[a] Time[e] (sec) | LRR[a] Dose[f] (mg/kg) | PWR = 1[b] Time[e] (sec) | PWR = 1[b] Dose[f] (mg/kg) | RRR[c] Time[e] (sec) | Walk[d] Time[e] (sec) |
|---|---|---|---|---|---|---|
| rac-ketamine | 59 ± 5 | 20 ± 2 | 93 ± 8 | 31 ± 2 | 863 ± 153 | 1918 ± 518 |
| (S)-C3OAc | 81 ± 10 | 26 ± 3 | 104 ± 7 | 34 ± 1 | 566 ± 30 | 983 ± 93 |
| rac-ketamine | 77 ± 10 | 27 ± 4 | 95 ± 13 | 38 ± 10 | 1602 ± 549 | 2536 ± 250 |
| rac-C2Et | 135 ± 61 | 48 ± 23 | 154 ± 68 | 55 ± 25 | 177 ± 51 | 253 ± 68 |
| rac-ketamine | 53 ± 1 | 20 ± 1 | 73 ± 3 | 26 ± 1 | 1315 ± 215 | 2163 ± 722 |
| (S)-C2Et | 171 ± 54 | 59 ± 19 | 185 ± 55 | 62 ± 20 | 62 ± 8 | 80 ± 8 |
| rac-ketamine | 62 ± 7 | 22 ± 2 | 71 ± 9 | 24 ± 3 | 760 ± 144 | 1100 ± 144 |
| rac-C2iPr | 103 ± 17 | 33 ± 6 | 127 ± 13 | 37 ± 6 | 83 ± 19 | 153 ± 33 |
| rac-ketamine | 65 ± 10 | 30 ± 4 | 77 ± 12 | 34 ± 4 | 900 ± 60 | 1200 ± 180 |
| (S)-C2iPr | 222 ± 18 | 74 ± 9 | 247 ± 13 | 84 ± 4 | 15 ± 15 | 224 ± 90 |
| rac-ketamine | 53 | 24 | 69 | 26 | 1170 | 1629 |
| (R)-C2iPr | 170 | 71 | 190 | 82 | 0 | 900 |
| rac-ketamine | 51 ± 3 | 18 ± 1 | 63 ± 3 | 21 ± 1 | 1060 ± 221 | 1500 ± 5 |
| rac-C2nPr | 404 ± 196 | 131 ± 62 | 420 ± 180 | 136 ± 67 | 0 | 0 |
| rac-ketamine | 59 ± 6 | 17 ± 2 | 76 ± 7 | 24 ± 4 | 1523 ± 131 | 2122 ± 131 |
| rac-C3Et | 70 ± 6 | 24 ± 2 | 137 ± 14 | 44 ± 5 | 95 ± 12 | 170 ± 17 |
| rac-ketamine | 69 ± 7 | 23 ± 2 | 84 ± 4 | 28 ± 2 | 874 ± 81 | 1384 ± 374 |
| rac-C3iPr | 125 ± 21 | 42 ± 9 | 192 ± 47 | 66 ± 17 | 37 ± 22 | 110 ± 45 |
| rac-ketamine | 69 ± 7 | 23 ± 2 | 84 ± 4 | 28 ± 2 | 874 ± 81 | 1384 ± 374 |
| rac-C3nPr | 329 ± 106 | 137 ± 48 | 558 ± 42 | 209 ± 20 | 10 ± 5.5 | 65 ± 33 |
| rac-ketamine | 70 ± 28 | 20 ± 5 | 81 ± 23 | 22 ± 4 | 1104 ± 95 | 1462 ± 113 |
| rac-C4Me | 92 ± 14 | 34 ± 7 | 124 ± 21 | 44 ± 10 | 99 ± 16 | 126 ± 32 |
| rac-ketamine | 56 ± 6 | 17 ± 2 | 76 ± 7 | 23 ± 4 | 1523 ± 131 | 2122 ± 107 |
| rac-C4Et | 97 ± 8 | 34 ± 4 | 172 ± 36 | 57 ± 12 | 134 ± 22 | 158 ± 22 |
| rac-ketamine | 54 | 19 | 66 | 22 | 1281 | 1499 |
| rac-C4iPr | 122 | 38 | 122 | 38 | 180 | 320 |
| rac-ketamine | 65 ± 10 | 23 ± 3 | 77 ± 12 | 26 ± 4 | 900 ± 60 | 1200 ± 180 |
| rac-C4nPr | 271 ± 97 | 82 ± 34 | 277 ± 97 | 83 ± 34 | 45 ± 15 | 90 ± 30 |
| rac-ketamine | 60 | 21 | 69 | 25 | 1230 | 1475 |
| 19 | 280 | 95 | 290 | 99 | 0 | 0 |
| rac-ketamine | 75 | 25 | 86 | 29 | 1500 | 1920 |
| 20 | 600 | 196 | 600 | 196 | 0 | 0 |
| rac-ketamine | 57 | 20 | 82 | 28 | 2040 | 2340 |
| 21 | 420 | 145 | 435 | 148 | 0 | 201 |

[a]LRR: (Loss of righting reflex) assesses anaesthetic effect. Righting reflex is considered absent when the animal fails to right from a position of dorsal recumbency to a position of sternal recumbency on three attempts performed in rapid succession.
[b]PWR (Pedal withdrawal reflex) assesses analgesic effect, and is conducted by a 1 second application of firm constant pressure (for rats, firm digital pressure) over the forepaw of the animal. A PWR = 1 (a flicker of response) indicates a satisfactory level of analgesia (nociception).
[c]RRR (Recovery of righting reflex; ability to right from dorsal recumbency).
[d]Walk (ability to sustain independent locomotion).
[e]Time: the time from onset of the infusion of drug to achieve LRR or PWR = 1, or the time from the end of the infusion of drug to achieve RRR or Walk.
[f]Dose: The total drug administered to achieve LRR or PWR = 1. Where no errors are given the results are from a single animal.

TABLE 3

Head-to-head ratios of anaesthetic effects of compounds of the invention to ketamine

| Compd | LRR[a] Time[e] | LRR[a] Dose[f] | PWR = 1[b] Time[e] | PWR = 1[b] Dose[f] | RRR[c] Time[e] | Walk[d] Time[e] |
|---|---|---|---|---|---|---|
| (S)-C3OAc | 1.37 | 1.30 | 1.12 | 1.10 | 0.65 | 0.51 |
| rac-C2Et | 1.75 | 1.78 | 1.62 | 1.45 | 0.11 | 0.10 |
| (S)-C2Et | 3.22 | 2.95 | 2.53 | 2.38 | 0.05 | 0.04 |
| rac-C2iPr | 1.66 | 1.50 | 1.79 | 1.54 | 0.11 | 0.14 |
| (S)-C2iPr | 3.41 | 2.46 | 3.14 | 2.47 | 0.02 | 0.19 |
| (R)-C2iPr | 3.20 | 2.96 | 2.75 | 3.15 | NA[g] | 0.06 |
| rac-C2nPr | 7.92 | 7.28 | 6.67 | 6.48 | NC[h] | NC[h] |
| rac-C3Et | 1.19 | 1.41 | 1.80 | 1.83 | 0.062 | 0.08 |
| (S)-C3Et | 3.23 | 2.95 | 2.53 | 2.38 | 0.05 | 0.04 |
| rac-C3iPr | 1.81 | 1.83 | 2.29 | 2.36 | 0.042 | 0.08 |
| rac-C3nPr | 4.77 | 5.95 | 6.64 | 7.46 | 0.012 | 0.05 |
| rac-C4Me | 1.31 | 1.70 | 1.53 | 2.00 | 0.090 | 0.086 |
| (S)-C4Me | 1.94 | 1.80 | 1.81 | 1.76 | 0.07 | 0.51 |
| rac-C4Et | 1.73 | 2.00 | 2.26 | 2.48 | 0.09 | 0.05 |
| (S)-C4Et | 1.73 | 2.00 | 2.26 | 2.48 | 0.088 | 0.074 |
| rac-C4iPr | 2.26 | 2.00 | 1.85 | 1.73 | 1.78 | 1.17 |
| rac-C4nPr | 4.17 | 3.56 | 3.60 | 3.19 | 0.05 | 0.08 |
| 19 | 4.67 | 4.50 | 4.20 | 3.96 | NC[h] | NC[h] |
| 20 | 8.00 | 7.84 | 6.98 | 6.76 | NC[h] | NC[h] |
| 21 | 7.37 | 7.25 | 5.30 | 5.29 | NC[h] | 0.09 |

[a-f]As for Table 2.
[g]NA: not active.
[h]NC: not calculable.

The results of Tables 2 and 3 clearly show that compounds of the invention show ketamine-like anaesthetic effects with similarly rapid onset and potency, but with much more rapid (up to 10-fold faster than ketamine) recovery following discontinuation of infusion.

The average values of the parameters measured for the ketamine standard over the various experiments is shown below in Table 4. Given the complexity of the experimental protocol, the pre-sedation data (time and total dose for LRR; Table 2) are very consistent, with ranges of only 1.5-fold. The consistency of the post-sedation recovery times are expectedly lower, with ranges of about 2.5-fold.

Figure 1B:
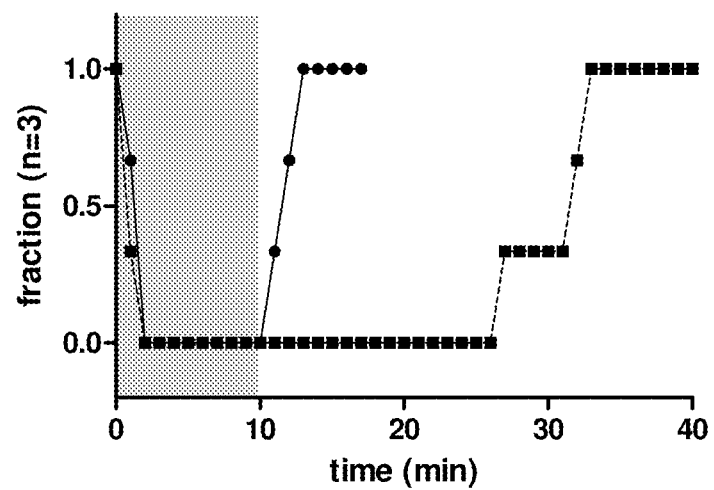
Figure 2A:
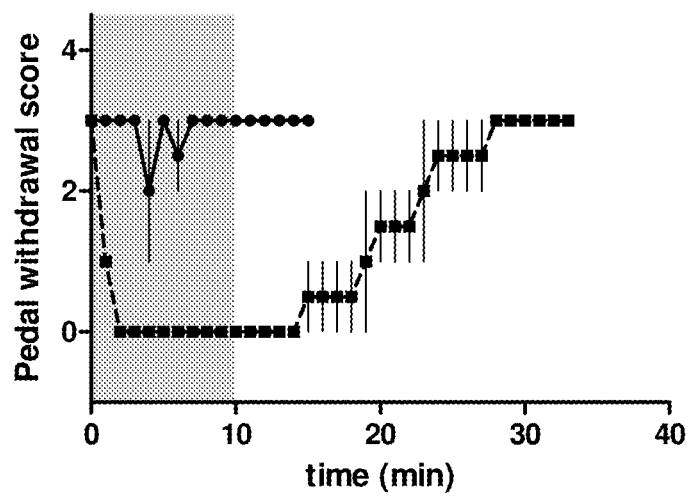
FIG. 2A and FIG. 2B are graphs showing time-course for analgesia (pedal withdrawal reflex score) with ketamine and rac-C2nPr (FIG. 2A) and rac-C4Me (FIG. 2B). The grey panel shows the duration of drug infusion (measurement taken every minute). Error bars are SEM. ••••: test compound. ■■■■ ketamine.
Figure 2B:
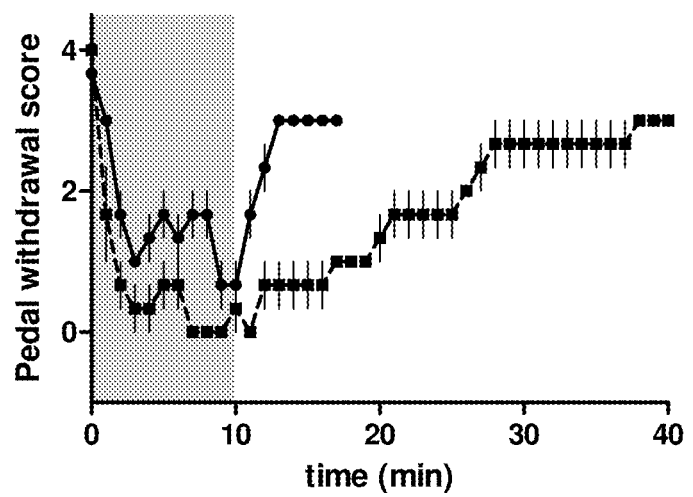

Representative plots of the performance of two representative compounds of the invention compared to ketamine in are shown in FIGS. 1 and 2. Loss of righting (anaesthesia) for rac-C2nPr and rac-C4Me are shown in FIGS. 1A and 1B, respectively, and pedal withdrawal scores are shown in FIGS. 2A and 2B.

Figure 3:
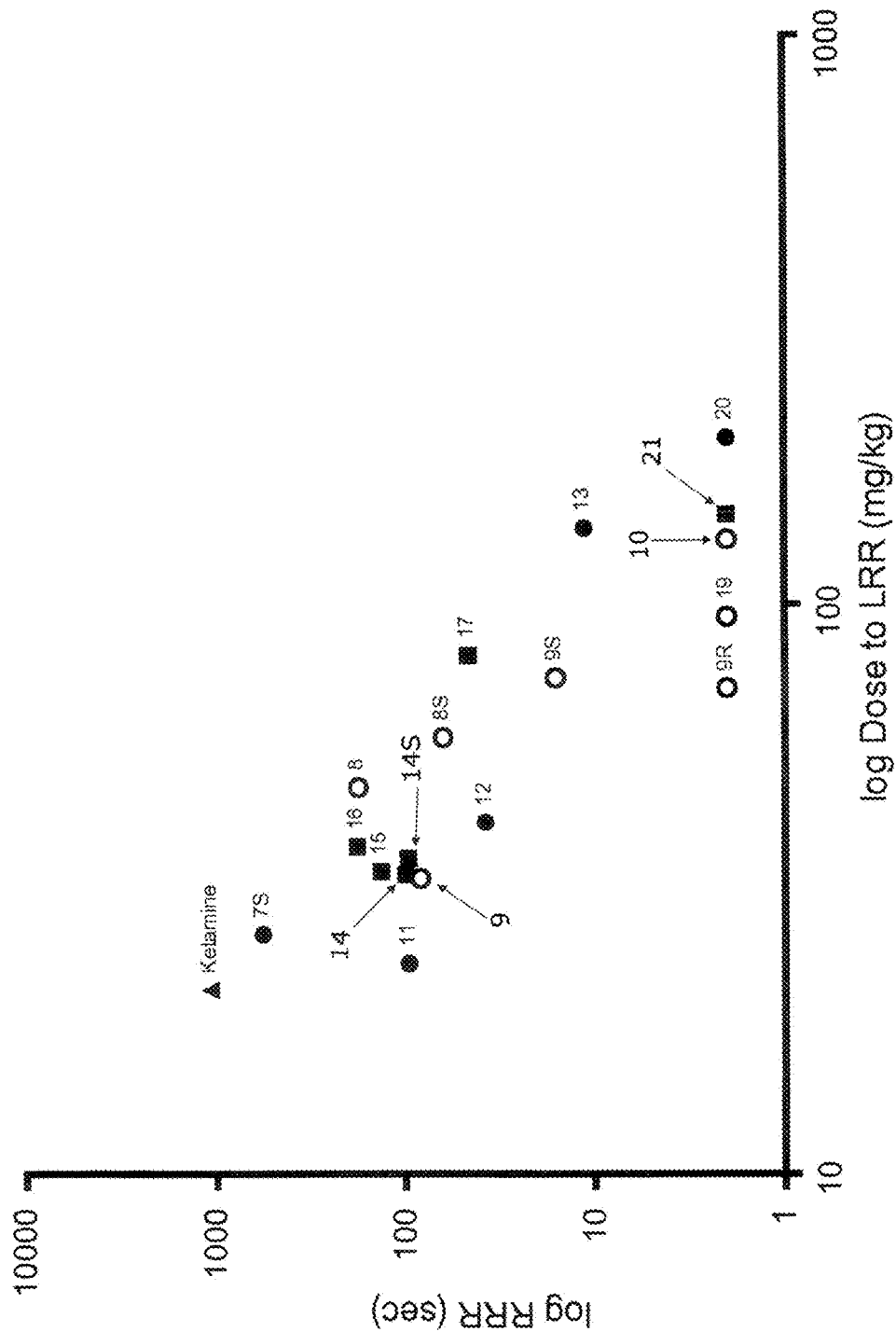
FIG. 3 is a plot (log 10) of effective potency (dose [mg/kg] to LRR) vs. duration (time to RRR) for ketamine and compounds of the invention. The alkyl chain length of compounds is denoted by symbol: ○=C2; ●=C3; ■=C4; ▲A=ketamine. 7=rac-C3OAc, 7S=(S)-C3OAC, 8=rac-C2Et, 8S=(S)-C2Et, 9=rac-C2iPr, 9S=(S)-C2iPr, 9R=(R)-C2iPr, 10=rac-C2nPr, 11=rac-C3Et, 12=rac-C3iPr, 13=rac-C3nPr, 14=rac-C4Me, 14S=(S)-C4Me, 15=rac-C4Et, 16=rac-C4iPr, and 17=rac-C4nPr.

FIG. 3 shows a scatter-plot of effective potency (dose [mg/kg] to loss of righting reflex) versus duration (time to return of righting reflex) for ketamine and representative compounds of the invention.

TABLE 4

Average parameters determined for the ketamine standard

| Property | Average | Range |
|---|---|---|
| Time to achieve LRR (sec) | 61 ± 8 | 51-75 |
| Total dose to LRR (mg/kg) | 21 ± 7 | 17-27 |
| Time to PWR = 1 (sec) | 76 ± 9 | 60-95 |
| Total dose to LRR (mg/kg) | 26 ± 4 | 21-34 |
| Time to RRR (sec) | 1212 ± 318 | 863-2040 |
| Time to walking (sec) | 1709 ± 400 | 1100-2340 |

DISCUSSION

Acetate (S)-C3OAc was the most potent of the compounds (about as potent as ketamine), but showed only moderately faster recoveries (1.5-2 fold) than ketamine itself. Without wishing to be bound by theory, the applicant believes that this is most likely not due to slow acetate hydrolysis, but to the fact that the corresponding alcohol product is itself a potent hypnotic/analgesic.

Of the remaining norketamine esters, the more potent compounds (up to 2-fold less dose-potent than ketamine itself) rac-C2Et, rac-C2iPr, rac-C3Et, rac-C3iPr, rac-C4Me, rac-C4Et and rac-C4iPr comprised a mixture of chain lengths (thus a range of pKas) and a variety of Me, Et and iPr esters.

The less dose-potent compounds (from 2-6 fold less than ketamine) rac-C2nPr, rac-C3nPr and rac-C4nPr were also a mixture of chain lengths, but were all n-Pr esters, and at the higher end of the lipophilicity range. Since dose-potency and rapidity of recovery from both LRR and PWR are broadly reciprocal, it is not surprising that these less potent compounds resulted in the fastest recoveries (20-25 fold faster than ketamine).

Most of the norketamine esters were racemic, but several enantiomers were evaluated, since (S)-ketamine is known to be as active but about twice as potent as its racemate. Two of the S-enantiomers ((S)-C2Et, (S)-C2iPr), while active, were only half as potent and showed faster recoveries than the corresponding racemates, suggesting more rapid hydrolysis of the S-enantiomer esters. The (R)-C2iPr enantiomer had similar potency and kinetics of recovery to (S)-C2iPr. rac-C4Me and enantiopure (S)-C4Me had broadly equivalent properties.

Exploratory studies were done (mostly single-animal evaluations) using ketamine esters 19-21. The racemic C2 ethyl ester 19 was about as potent as the n-Pr norketamine esters, but had a very weak sedative effect, with very rapid recovery. Longer chain length C3 ethyl and C4 methyl esters 20 and 21, were less potent, with weak sedative activity.

There was no clear effect of pKa on anaesthetic activity, although the weakest bases were among the least potent of the esters.

In summary, the above results show that short-chain aliphatic ester analogues of ketamine broadly retain its desirable anaesthetic and analgesic activities, yet are metabolised to the more polar and inactive acids sufficiently rapidly to minimise the drawbacks of ketamine itself in this capacity.

Although the invention has been described by way of example and with reference to particular embodiments, it is to be understood that modifications and/or variations may be made without departing from the scope of the invention.

All publications referenced in this specification are incorporated herein in their entirety.

The invention claimed is:

1. A compound of formula (I):

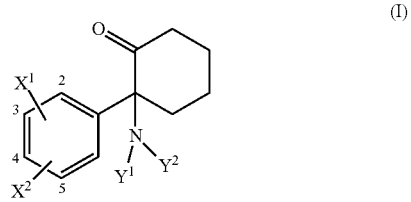

(I)

wherein
Y[1] is —C$_{2-6}$alkylC(O)OR[1], —C$_{2-6}$alkylOC(O)R[1], —C$_{1-6}$alkylC(O)OC$_{1-6}$alkylC(O)OR[1], or —C$_{1-6}$alkylC(O)OC$_{1-6}$alkylOR[3], wherein each alkyl is optionally substituted with one or more R[2];

R₁ is C₁₋₆aliphatic, optionally substituted with one or more halo, CN, NO₂, NH₂, NHR¹¹, NR¹¹R¹², C₁₋₆haloalkyl, C₁₋₆haloalkoxy, C(O)NH₂, C(O)NHR¹¹, C(O)NR¹¹R¹², SO₂R¹¹, OR¹¹, C(O)R¹¹, and C₁₋₆aliphatic;

R² is C₁₋₆aliphatic, optionally substituted with one or more halo, OR¹¹, or CN;

R³ is hydrogen or R¹;

R¹¹ and R¹² are each independently C₁₋₆aliphatic; or R¹¹ and R¹² together with the nitrogen atom to which they are attached are a heteroaryl or heterocyclyl ring;

Y² is hydrogen or R²;

X¹ and X² are each independently hydrogen, R², halo, NO₂, NH₂, NHR¹¹, NR¹¹R¹², C₁₋₆haloalkyl, C₁₋₆haloalkoxy, C(O)NH₂, C(O)NHR¹¹, C(O)NR¹¹R¹², SO₂R¹¹, OR¹¹, C(O)R¹¹, C₁₋₆aliphaticY¹, OY¹, C(O)Y¹, SO₂Y¹, or C(O)NHY¹ at any of the available 2-5 positions;

or a pharmaceutically acceptable salt or solvate thereof.

2. The compound of claim 1, wherein Y¹ is —C₂₋₆alkylC(O)OR¹ or —C₂₋₆alkylOC(O)R¹, wherein each alkyl is optionally substituted.

3. The compound of claim 1, wherein Y¹ is —C₂₋₆alkylC(O)OR¹, wherein the alkyl is optionally substituted.

4. The compound of claim 1, wherein R¹ is C₁₋₆alkyl, C₂₋₆alkenyl, cycloalkyl, or cycloalkenyl, wherein each alkyl and cycloalkyl are optionally substituted with one or more halo, CN, NO₂, NH₂, NHR¹¹, NR¹¹R¹², C₁₋₆haloalkyl, C₁₋₆haloalkoxy, C(O)NH₂, C(O)NHR¹¹, C(O)NR¹¹R¹², SO₂R¹¹, OR¹¹, and C(O)R¹¹; and each alkyl is optionally substituted with cycloalkyl or cycloalkenyl; and each cycloalkyl is optionally substituted with C₁₋₆alkyl or C₂₋₆alkenyl.

5. The compound of claim 4, wherein R¹ is C₁₋₆alkyl or cycloalkyl, wherein each alkyl and cycloalkyl is optionally substituted.

6. The compound of claim 5, wherein R¹ is C₁₋₆alkyl, wherein each alkyl is optionally substituted.

7. The compound of claim 1, wherein R² is C₁₋₆alkyl or cycloalkyl, optionally substituted with one or more halo, OR¹¹, or CN.

8. The compound of claim 7, wherein R² is C₁₋₆alkyl, optionally substituted with one or more halo, OR¹¹, or CN.

9. The compound of claim 1, wherein Y² is hydrogen or C₁₋₆alkyl, wherein the alkyl is optionally substituted.

10. The compound of claim 1, wherein and X¹ and X² are each independently hydrogen, R², halo, NO₂, NH₂, NHR¹¹, NR¹¹R¹², C₁₋₆haloalkyl, C₁₋₆haloalkoxy, C(O)NH₂, C(O)NHR¹¹, C(O)NR¹¹R¹², SO₂R¹¹, OR¹¹, or C(O)R¹¹; or X² is C₁₋₆alkyl, C(O)Y¹, SO₂Y¹, or C(O)NHY¹ at any of the available 2-5 positions.

11. The compound of claim 10, wherein X¹ and X² are each independently hydrogen, R², halo, C₁₋₆haloalkyl, C₁₋₆haloalkoxy, SO₂R¹¹, or OR¹¹ at any of the available 2-5 positions.

12. The compound of claim 11, wherein X¹ is 2-chloro; and X² is hydrogen, R², halo, C₁₋₆haloalkyl, C₁₋₆haloalkoxy, SO₂R¹¹, or OR¹¹ at any of positions 3-5.

13. The compound of claim 1, wherein Y¹ is —(CR^A R^B)_m(CR^C R^D)_n C(O)OR¹, —(CR^A R^B)_m(CR^C R^D)_n OC(O)R¹, —(CR^A R^B)_{m-1}(CR^C R^D)_n C(O)O(CR^G R^H)_p(CR^E R^F)_o C(O)OR¹, or —(CR^A R^B)_{m-1}(CR^C R^D)_n C(O)O(CR^G R^H)_p(CR^E R^F)_o OR³; m is an integer from 2 to 6; o is an integer from 1 to 6; n and p are each independently 0 or 1; the sum of m and n and the sum of o and p is 6 or less; and R^A, R^B, R^C, R^D, R^E, R^F, R^G, and R^H at each instance of m, n, o, and p are each independently hydrogen or R².

14. The compound of claim 13, wherein Y¹ is —(CR^A R^B)_m(CR^C R^D)_n C(O)OR¹.

15. The compound of claim 13, wherein R^A, R^B, R^E, and R^F at each instance of m and o are each independently hydrogen; and R^C, R^D, R^G, and R^H at each instance of n and p are each independently hydrogen or R².

16. The compound of claim 1, wherein the compound is
3-((1-(2-chlorophenyl)-2-oxocyclohexyl)amino)propyl acetate,
ethyl 3-((1-(2-chlorophenyl)-2-oxocyclohexyl)amino) propanoate,
iso-propyl 3-((1-(2-chlorophenyl)-2-oxocyclohexyl) amino) propanoate,
n-propyl 3-((1-(2-chlorophenyl)-2-oxocyclohexyl)amino) propanoate,
ethyl 4-((1-(2-chlorophenyl)-2-oxocyclohexyl)amino) butanoate,
isopropyl 4-((1-(2-chlorophenyl)-2-oxocyclohexyl) amino) butanoate,
n-propyl 4-((1-(2-chlorophenyl)-2-oxocyclohexyl)amino) butanoate,
methyl 5-((1-(2-chlorophenyl)-2-oxocyclohexyl)amino) pentanoate,
ethyl 5-((1-(2-chlorophenyl)-2-oxocyclohexyl)amino) pentanoate,
isopropyl 5-((1-(2-chlorophenyl)-2-oxocyclohexyl) amino) pentanoate,
n-propyl 5-((1-(2-chlorophenyl)-2-oxocyclohexyl)amino) pentanoate,
ethyl 3-((1-(2-chlorophenyl)-2-oxocyclohexyl)(methyl) amino) propanoate,
ethyl 4-((1-(2-chlorophenyl)-2-oxocyclohexyl)(methyl) amino) butanoate, or
methyl 5-((1-(2-chlorophenyl)-2-oxocyclohexyl)(methyl) amino) pentanoate, or
a pharmaceutically acceptable salt or solvate thereof.

17. A pharmaceutical composition comprising a compound of formula (I) or a pharmaceutically acceptable salt or solvate thereof according to claim 1, and a pharmaceutically acceptable diluent, excipient, or carrier.

18. A method for treating pain in a subject in need thereof, the method comprising administering a therapeutically effective amount of a compound of formula (I) or a pharmaceutically acceptable salt or solvate thereof according to claim 1 to the subject.

19. The compound of claim 1, wherein X1 is 2-halo and X2 is hydrogen.

20. The compound of claim 1, wherein Y2 is hydrogen or methyl.

21. The compound of claim 1, wherein R1 is C1-6alkyl.

22. The compound of claim 1, wherein X1 is 2-chloro and X2 is hydrogen.

23. The compound of claim 1, wherein the compound is methyl 5-((1-(2-chlorophenyl)-2-oxocyclohexyl)amino) pentanoate, or a pharmaceutically acceptable salt or solvate thereof.

24. The compound of claim 1, wherein the compound is isopropyl 3-((1-(2-chlorophenyl)-2-oxocyclohexyl)amino) propanoate, or a pharmaceutically acceptable salt or solvate thereof.

* * * * *